(12) United States Patent
Heneka et al.

(10) Patent No.: US 9,011,862 B2
(45) Date of Patent: Apr. 21, 2015

(54) INHIBITORS OF THE NITRATION OF AMYLOID β PEPTIDES AND THEIR USES IN THE DIAGNOSIS AND TREATMENT OF ALZHEIMER'S DISEASE

(75) Inventors: Michael Thomas Heneka, Bonn (DE); Markus Peter Kummer, Grafschaft (DE)

(73) Assignee: Rheinische Friedrich-Wilhelms-Universität Bonn, Bonn (DE)

( * ) Notice: Subject to any disclaimer, the term of this patent is extended or adjusted under 35 U.S.C. 154(b) by 216 days.

(21) Appl. No.: 13/383,521

(22) PCT Filed: Jul. 12, 2010

(86) PCT No.: PCT/EP2010/059984
§ 371 (c)(1),
(2), (4) Date: Mar. 29, 2012

(87) PCT Pub. No.: WO2011/006871
PCT Pub. Date: Jan. 20, 2011

(65) Prior Publication Data
US 2012/0192294 A1 Jul. 26, 2012

(30) Foreign Application Priority Data
Jul. 11, 2009 (EP) .................................. 09009085

(51) Int. Cl.
*A61K 39/395* (2006.01)
*G01N 33/68* (2006.01)
*C07K 14/47* (2006.01)
*C07K 16/18* (2006.01)
*A61K 39/00* (2006.01)

(52) U.S. Cl.
CPC ........ *G01N 33/6896* (2013.01); *C07K 14/4711* (2013.01); *C07K 16/18* (2013.01); *A61K 2039/505* (2013.01); *G01N 2333/90254* (2013.01); *G01N 2800/2821* (2013.01)

(58) Field of Classification Search
CPC .................... A61K 2039/505; C07K 14/4711; C07K 16/18; G01N 2800/2821; G01N 33/6896; G01N 2333/90254
See application file for complete search history.

(56) References Cited

U.S. PATENT DOCUMENTS

| | | | |
|---|---|---|---|
| 6,506,782 B1 | 1/2003 | Thorsett et al. | |
| 8,491,890 B2 * | 7/2013 | Gendelman et al. | 424/94.4 |
| 2002/0104104 A1 * | 8/2002 | Games et al. | 800/3 |
| 2006/0240486 A1 | 10/2006 | Johnson-Wood et al. | |
| 2007/0098721 A1 | 5/2007 | Hillen et al. | |

FOREIGN PATENT DOCUMENTS

| | | |
|---|---|---|
| EP | 2009445 | 12/2008 |
| WO | WO 96/39834 | 12/1996 |
| WO | WO 99/26657 | 6/1999 |
| WO | WO 01/39796 | 6/2001 |
| WO | WO 01/42266 | 6/2001 |
| WO | WO 03/074081 | 9/2003 |
| WO | WO 2004/067561 | 8/2004 |
| WO | WO 2007/108756 | 9/2007 |

OTHER PUBLICATIONS

Lee et al., J. Biol. Chem. 2006, 281:4292-4299.*
Atwood et al., "Neurotoxic Aβ Oligomers Derived from Alzheimer Amyloid are Cross-linked at Tyrosine", *Abstracts of the Annual Meeting of the Society for Neuroscience*, Society for Neuroscience, Washington, DC, 2000, vol. 26, No. 1/02, Accession No: XP008063742.
Bard et al., "Epitope and isotype specificities of antibodies β-amyloid peptide for protection against Alzheimer's disease-like neuropathology", *Proceedings of the National Academy of Sciences of the United States of America*, 2003, vol. 100, No. 4, pp. 2023-2028.
Castenga et al., "Proteomic identification of nitrated proteins in Alzheimer's disease brain", *Journal of Neurochemistry*, 2003, vol. 85, No. 6, pp. 1394-1401.
Colton et al., "NO synthase 2 (NOS2) deletion promotes multiple pathologies in a mouse model of Alzheimer's disease", *Proceedings of the National Academy of Sciences of the United States of America*, 2006, vol. 103, No. 34, pp. 12867-12872.
Colton et al., "The Effects of NOS2 Gene Deletion on Mice Expressing Mutated Human AβPP", *Journal of Alzheimer's Disease*, 2008, vol. 15, No. 4, pp. 571-587.
Good et al., "Evidence for Neuronal Oxidative Damage in Alzheimer's Disease", *The American Journal of Pathology*, 1996, vol. 149, No. 1, pp. 21-28.

(Continued)

*Primary Examiner* — Doug Schultz
(74) *Attorney, Agent, or Firm* — Saliwanchik, Lloyd & Eisenschenk

(57) ABSTRACT

The present invention relates to a method for identifying an inhibitor of the aggregation of amyloid-β peptide (Aβ), comprising the steps of a) contacting at least one Aβ -peptide and/or the nitrated forms thereof with at least one candidate inhibitor that potentially specifically binds to a region in said Aβ -peptide capable of being nitrated, and b) detecting said inhibitor specifically binding to said region in said Aβ -peptide through detecting a lack of or a reduced aggregation of said at least one Aβ -peptide. The present invention is further directed at improved methods for treating neuronal degradation and particularly Alzheimer's disease, based on said inhibitor. The present invention is further directed at methods for diagnosing the aggregation of Aβ -peptide in the context of neuronal degradation and particularly Alzheimer's disease.

4 Claims, 30 Drawing Sheets

(56) References Cited

OTHER PUBLICATIONS

Figure 1A:
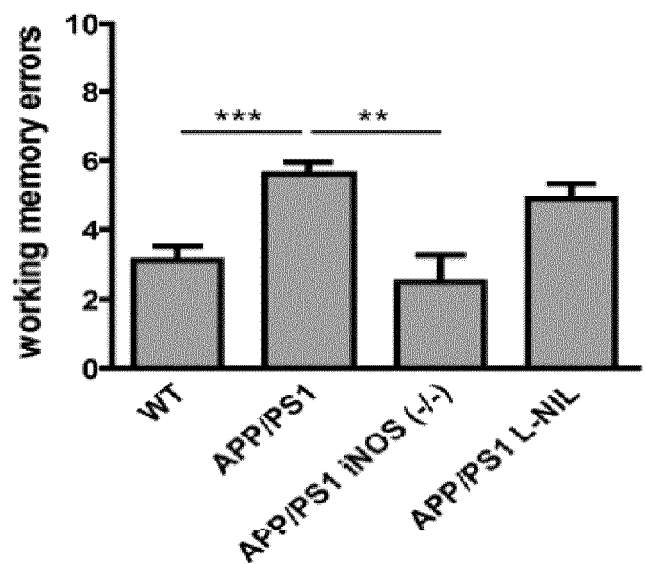
Figure 1B:
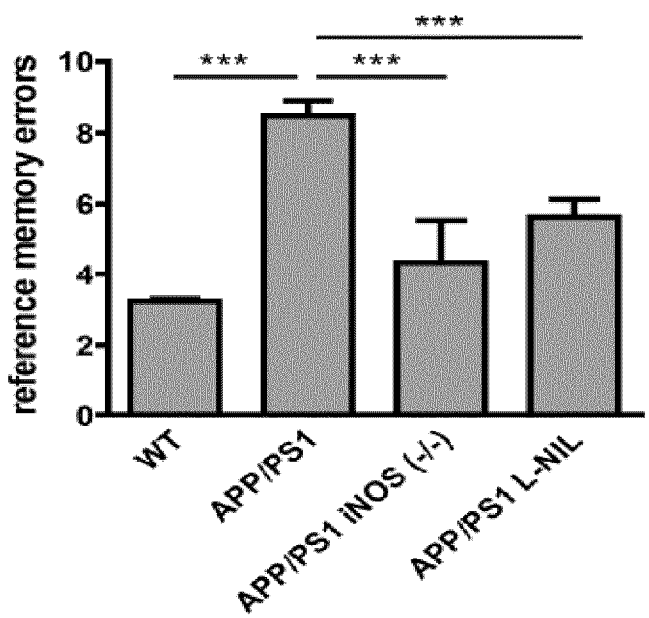

Nathan et al., "Protection from Alzheimer's-like disease in the mouse by genetic ablation of inducible nitric oxide synthase", *The Journal of Experimental Medicine*, 2005, vol. 202, No. 9, pp. 1163-1169.

Praticó et al., "Oxidative stress hypothesis in Alzheimer's disease: a reappraisal", *Trends in Pharmacological Sciences*, 2008, vol. 29, No. 12, pp. 609-615.

Seyidova et al., "The Role of Nitric Oxide in the Pathogenesis of Brain Lesions During the Development of Alzheimer's Disease", in vivo, 2004, vol. 18, No. 3, pp. 325-334.

* cited by examiner

```
          10         20         30         40         50         60
MISASRAAAA RLVGTAASRS PAAARPQDGW NGLSHEAFRF VSRRDYASEA IKGAVVGIDL
          70         80         90        100        110        120
GTTNSCVAVM EGKQAKVLEN AEGARTTPSV VAFTADGERL VGMPAKRQAV TNPNNTFYAT
         130        140        150        160        170        180
KRLIGRRYDD PEVQKDTKNV PFKIVRASNG DAWVEAHGKL YSPSQIGAFV LMKMKETAEN
         190        200        210        220        230        240
YLGHTAKNAV ITVPAYFNDS QRQATKDAGQ ISGLNVLRVI NEPTAAALAY GLDKSEDKVI
         250        260        270        280        290        300
AVYDLGGGTF DISILEIQKG VFEVKSTNGD TFLGGEDFDQ ALLRHIVKEF KRETGVDLTK
         310        320        330        340        350        360
DNMALQRVRE AAEKAKCELS SSVQTDINLP YLTMDASGPK HLNMKLTRAQ FEGIVTDLIK
         370        380        390        400        410        420
RTIAPCQKAM QDAEVSKSDI GEVILVGGMT RMPKVQQTVQ DLFGRAPSKA VNPDEAVAIG
         430        440        450        460        470        480
AAIQGGVLAG DVTDVLLLDV TPLSLGIETL GGVFTKLINR NTTIPTKKSQ VFSTAADGQT
         490        500        510        520        530        540
QVEIKVCQGE REMAGDNKLL GQFTLIGIPP APRGVPQIEV TFDIDANGIV HVSAKDKGTG
         550        560        570        580        590        600
REQQIVIQSS GGLSKDDIEN MVKNAEKYAE EDRRKKERVE AVNMAEGIIH DTETKMEEFK
         610        620        630        640        650        660
DQLFADECNK LKEEISKVRA LLARKDSETG ENIRQAASSL QQASLKLFEM AYKKMASERE
         670
GSGSSGTGEQ KEDQKEEKQ  (SEQ ID NO:6)
```

FIG. 2E

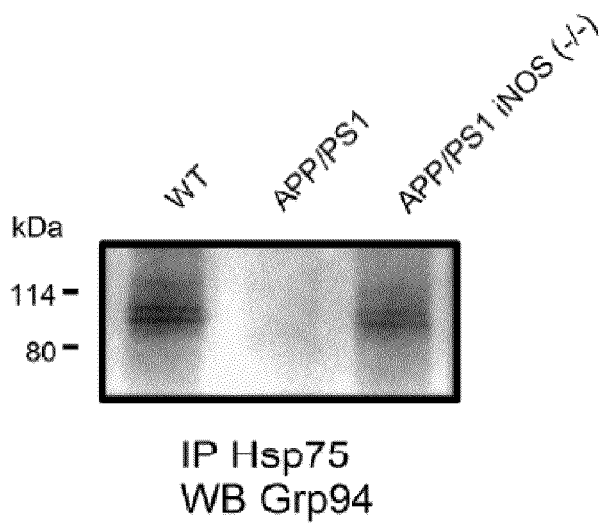

IP Hsp75
WB Grp94

FIG. 2F

SEQUENCE LISTING

```
<160> NUMBER OF SEQ ID NOS: 5

<210> SEQ ID NO 1
<211> LENGTH: 42
<212> TYPE: PRT
<213> ORGANISM: homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 42
<212> TYPE: PRT
<213> ORGANISM: artificial sequence
<220> FEATURE:
<223> OTHER INFORMATION: Human Abeta peptide containing a Y to A
      mutation at position 10

<400> SEQUENCE: 2

Asp Ala Glu Phe Arg His Asp Ser Gly Ala Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 42
<212> TYPE: PRT
<213> ORGANISM: mus musculus

<400> SEQUENCE: 3

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30
```

```
Gly Leu Met Val Gly Gly Val Val Ile Ala
        35                  40

<210> SEQ ID NO 4
<211> LENGTH: 12
<212> TYPE: PRT
<213> ORGANISM: homo sapiens

<400> SEQUENCE: 4

Phe Arg His Asp Ser Gly Tyr Glu Val His His Gln
1               5                   10

<210> SEQ ID NO 5
<211> LENGTH: 11
<212> TYPE: PRT
<213> ORGANISM: artificial sequence
<220> FEATURE:
<223> OTHER INFORMATION: Region of human Abeta peptide containing a Y
      to E mutation at position 10

<400> SEQUENCE: 5

Phe Arg His Asp Ser Gly Glu Val His His Gln
1               5                   10
```

INHIBITORS OF THE NITRATION OF AMYLOID β PEPTIDES AND THEIR USES IN THE DIAGNOSIS AND TREATMENT OF ALZHEIMER'S DISEASE

CROSS REFERENCE TO A RELATED APPLICATION

This application is a National Stage Application of International Application Number PCT/EP2010/059984, filed Jul. 12, 2010; which claims priority to European Patent Application No. 09009085.3, filed Jul. 11, 2009; all of which are incorporated herein by reference in their entirety.

The Sequence Listing for this application is labeled "SeqList-30Jan15.txt," which was created on Jan. 30, 2015, and is 8 KB. The entire content is incorporated herein by reference in its entirety.

The present invention relates to a method for identifying an inhibitor of the aggregation of amyloid-β peptide (Aβ), comprising the steps of a) contacting at least one Aβ-peptide and/or the nitrated forms thereof with at least one candidate inhibitor that potentially specifically binds to a region in said Aβ-peptide capable of being nitrated, and b) detecting said inhibitor specifically binding to said region in said Aβ-peptide through detecting a lack of or a reduced aggregation of said at least one Aβ-peptide. The present invention is further directed at improved methods for treating neuronal degradation and particularly Alzheimer's disease, based on said inhibitor. The present invention is further directed at methods for diagnosing the aggregation of Aβ-peptide in the context of neuronal degradation and particularly Alzheimer's disease.

BACKGROUND OF THE INVENTION

Alzheimer's disease (AD) is clinically characterized by progressive memory loss and decline of cognitive functions and histopathologically by extracellular deposition of fragments (amyloid β (Aβ) peptides) of the amyloid precursor protein and intracellular deposits of hyperphosphorylated tau protein in neurofibrillary tangles. These fragments are generated by subsequent cleavages of two aspartic proteases BACE1 and presenilin 1, resulting in the liberation of Aβ peptides of various lengths (Aβ 1-38/40/42).

There is evidence that formation of, in particular, aggregated Aβ 1-42 contributes to synaptic dysfunction and oxidative stress that results in neuronal degeneration. One source of the oxidative stress is the formation of oxidative species arising from the conversion of nitric oxide to peroxynitrite.

The NOS2 gene encoding the inducible form of the nitric oxide synthase (iNOS) is one of three NOS proteins that generate NO in the brain. It has been shown that iNOS is upregulated in neurons and astrocytes in response to degenerative and inflammatory stimuli in Alzheimer's disease, potentially aggravating disease progression[2,3]. Despite potentially being involved in the aggravating of disease progression in AD, iNOS is a pro-inflammatory mediator that is upregulated not only in AD, but in many age-related diseases (see, e.g., Chung H Y, Cesari M, Anton S, Marzetti E, Giovannini S, Seo A Y, Carter C, Yu B P, Leeuwenburgh C. Molecular inflammation: underpinnings of aging and age-related diseases. Ageing Res Rev. 2009 January; 8(1):18-30. Epub 2008 Jul. 18).

iNOS produces large amounts of NO for prolonged periods of time resulting in reactive nitrogen intermediates and thereby exerts effects on mitochondrial respiration[4], enzyme activity[5] neuronal cell death[6-9] and induction of apoptosis[10].

AD lesions reveal the pathological pattern of oxidative and nitrosative injury, especially the posttranslational modifications of cysteine and tyrosine residues[11-15]. One of the modifications is S-nitrosylation, or covalent reaction of NO with specific protein thiol groups, leading to protein misfolding and neurotoxicity[16]. In addition, conversion of protein tyrosine residues to 3'-nitrotyrosine have been found under pathological conditions and result in changes in enzyme activities, protein degradation and immune responses[17].

Furthermore, it appears that an immunization using Aβ 1-42 resulted in a clearance of amyloid plaques in patients with AD, but this clearance did not prevent progressive neurodegeneration (Holmes C, Boche D, Wilkinson D, Yadegarfar G, Hopkins V, Bayer A, Jones R W, Bullock R, Love S, Neal J W, Zotova E, Nicoll J A. Long-term effects of Abeta42 immunisation in Alzheimer's disease: follow-up of a randomized, placebo-controlled phase I trial. Lancet. 2008 Jul. 19; 372(9634):216-23). Thus, it is under discussion in the state of the art whether an anti-amyloid therapy would improve the situation in patients.

Attempts have been undertaken to improve the situation in AD using anti-inflammatory agents, but the clinical trials failed.

WO 99/26657 and WO 98/09653 describe iNOS inhibitors and their prospective uses in, amongst others, AD. U.S. Pat. No. 7,300,955 describes the combined use of an inhibitor of formation or release of β-amyloid and a nitric oxide releaser for the treatment or prevention of Alzheimer's disease. U.S. Pat. No. 7,371,770 describes the use of an inhibitor of the formation of β-amyloid peptide in the treatment of AD.

In summary, researchers in Alzheimer's disease have identified five strategies as possible interventions against amyloid:

a) β-Secretase inhibitors. These work to block the first cleavage of APP outside of the cell.

b) γ-Secretase inhibitors (e.g. Semagacestat). These work to block the second cleavage of APP in the cell membrane and would then stop the subsequent formation of Aβ and its toxic fragments.

c) Selective $A\beta_{42}$ lowering agents (e.g. Tarenflurbil). These modulate γ-secretase to reduce $A\beta_{42}$ production in favor of other (shorter) Aβ versions.

d) Immunotherapies. These stimulate the host immune system to recognize and attack Aβ or provide antibodies that either prevent plaque deposition or enhance clearance of plaques.

e) Anti-aggregation agents based on the chemical structure of apomorphine. These molecules were found to interfere with Aβ1-40 fibrillization through oxidative processes (Lashuel H A, Hartley D M, Balakhaneh D, Aggarwal A, Teichberg S, Callaway D J E (2002). "New class of inhibitors of amyloid-beta fibril formation. Implications for the mechanism of pathogenesis in Alzheimer's disease". *J Biol Chem* 277 (45): 42881-42890). These prevent Aβ fragments from aggregating or clear aggregates once they are formed (Michael H. Parker, Robert Chen, Kelly A. Conway, Daniel H. S. Lee; Chi Luoi, Robert E. Boyd, Samuel O. Nortey, Tina M. Ross, Malcolm K. Scott, Allen B. Reitz (2002). "Synthesis of (+)-5,8-Dihydroxy-3R-methyl-2R (dipropylamino)-1,2,3,4-tetrahydro-naphthalene: An Inhibitor of β-Amyloyid$_{1-42}$ Aggregation". *Bioorg. Med. Chem.* 10 (11): 3565-3569).

There is some indication that supplementation of the hormone melatonin may be effective against amyloid.

Despite the numerous attempts in the state of the art to identify effective targets to improve the situation with respect to the disease progression in AD, no satisfactory progresses have been made so far. It is therefore an object of the present invention, to provide such a new target that may serve as a promising approach for an improved treatment in AD. This target shall be used in assays to find new medicines for AD, and also to provide effective diagnostic assays for the disease. Further objects and advantages will become apparent to the person of skill when reading the following more detailed description of the present invention.

In a preferred first aspect of the present invention, the invention relates to a method for identifying an inhibitor of the aggregation of amyloid-β peptide (Aβ), comprising the steps of a) contacting at least one Aβ-peptide and/or the nitrated forms thereof with at least one candidate inhibitor that potentially specifically binds to a region in said Aβ-peptide capable of being nitrated, and b) detecting said inhibitor specifically binding to said region in said Aβ-peptide through detecting a lack of or a reduced aggregation of said at least one Aβ-peptide. Preferably, said Aβ-peptide is selected from 1-38, 1-40, and 1-42, and the nitrated forms thereof.

In a preferred second aspect of the present invention, the invention relates to a method for producing an antibody or fragment thereof that specifically binds to a region in an Aβ-peptide capable of being nitrated, in particular a 3NT10Aβ-antibody or fragment thereof, comprising the steps of a) affinity purification of a serum containing antibodies using a nitrated Aβ-peptide coupled to a chromatography column, or screening an sc-Fv phage display library using a nitrated Aβ-peptide, and b) optionally followed by a further purification step through exclusion of binding to a non-nitrated Aβ-peptide, such as a natural or recombinant Aβ-peptide lacking a tyrosine at position 10 thereof. The invention further relates to an anti-body or fragment thereof specifically binding to a region in an Aβ-peptide capable of being nitrated, in particular a 3NT10Aβ-antibody or fragment thereof, produced according to the method according to the present invention, wherein said antibody preferably is a monoclonal, polyclonal, human, humanized, and/or recombinant antibody or a functional fragment thereof.

The inhibitor of the aggregation of amyloid-β peptide according to the present invention is in a most preferred embodiment a substance specifically and exclusively interacting with the Aβ-peptide itself, preferably with a region in the Aβ-peptide capable of being nitrated, such as the tyrosine at position 10, thereby inhibiting Aβ-peptide nitration. Such an inhibitor is for example a specific antibody directed to the Aβ-peptide.

In a preferred third aspect of the present invention, the invention then relates to a pharmaceutical composition or formulation, and to a method for producing such a pharmaceutical composition, comprising an inhibitor as identified according to the present invention or an anti-body or fragment thereof according the present invention.

In a preferred fourth aspect of the present invention, the invention then relates to a recombinant non-human iNOS (−/−) mammal, in particular an APP iNOS (−/−) mouse, an APP (−/−) iNOS (−/−) mouse, or APP/PS-1 iNOS (−/−) mouse. Said animal can be used as a preferred advantageous "tool" in the context of the present invention.

In a still preferred fifth aspect of the present invention, the invention then relates to a diagnostic method for determining the status and/or progression of the aggregation of amyloid-β peptide (Aβ), comprising the steps of a) detecting the amount and/or fraction of nitrated amyloid-β peptide in a sample obtained from a patient to be diagnosed using an antibody or fragment thereof that specifically binds to a region in an Aβ-peptide capable of being nitrated, in particular a 3NT10Aβ-antibody or fragment thereof, b) comparing said amount and/or fraction of nitrated amyloid-β peptide as detected with a control sample, and, optionally, c) concluding on the status and/or progression of the aggregation of amyloid-β peptide (Aβ) based on said difference in the amount and/or fraction as detected between the sample and the control sample.

In a preferred sixth aspect of the present invention, the invention relates to a diagnostic kit, comprising an inhibitor as identified according to the present invention and/or an antibody or fragment thereof according to the present invention, optionally, together with additional auxiliary agents for performing a method according to an aspect of the present invention.

In a preferred seventh aspect of the present invention, the invention relates to an inhibitor as identified according to the present invention, an antibody or fragment thereof according to the present invention, an Aβ-peptide lacking a tyrosine at position 10 thereof, in particular a peptide selected from SEQ ID No. 2 or 3, or a pharmaceutical composition or formulation according to the present invention for use in the treatment of the aggregation of amyloid-β peptide (Aβ) and Alzheimers' disease.

Another embodiment of the above seventh aspect of the present invention relates to an Aβ-peptide lacking a tyrosine at position 10 thereof, in particular a peptide wherein the tyrosine at position 10 is substituted by an alanine or a phenylalanine, and respective pharmaceutical compositions and formulations thereof for use in the treatment of the aggregation of amyloid-β peptide (Aβ) and Alzheimers' disease.

In a preferred eighth aspect of the present invention, the invention then relates to a method for treating synaptic dysfunction and oxidative stress resulting in neuronal degeneration in a patient in need thereof, comprising administering a therapeutically effective amount of inhibitor as identified according to the present invention, an antibody or fragment thereof according to the present invention, an Aβ-peptide lacking a tyrosine at position 10 thereof, in particular a peptide selected from SEQ ID No. 2 or 3, or a pharmaceutical composition or formulation according to the present invention to said patient.

In the preferred ninth aspect of the present invention, the invention then finally relates to a method for improving cognitive functions in a patient suffering from neuronal degeneration, in particular from Alzheimers' disease, comprising administering a therapeutically effective amount of inhibitor as identified according to the present invention, an antibody or fragment thereof according to the present invention, an Aβ-peptide lacking a tyrosine at position 10 thereof, in particular a peptide selected from SEQ ID No. 2 or 3, or a pharmaceutical composition or formulation according to the present invention to said patient.

The present invention provides a method for identifying an inhibitor of the aggregation of amyloid-β peptide (Aβ), comprising the steps of a) contacting at least one Aβ-peptide and/or the nitrated forms thereof with at least one candidate inhibitor that potentially specifically binds to a region in said Aβ-peptide capable of being nitrated, and b) detecting said inhibitor specifically binding to said region in said Aβ-peptide through detecting a lack of or a reduced aggregation of said at least one Aβ-peptide.

The amino acid sequence of the human Aβ-peptide reads: DAEFRHDSG<u>Y</u>EVHHQKLVFFAEDVGSNKGAIIGLMVGGVVIA (SEQ ID NO. 1). This peptide comprises a site for nitration at the tyrosine at position 10 (bold and underlined). The fragments are generated from the (human) Aβ-precursor protein (APP) by subsequent cleavage of two aspartic proteases BACE1 and presenilin 1, resulting in the liberation of Aβ peptides of various lengths (Aβ 1-38/40/42). Thus, preferred is a method according to the present invention, wherein said Aβ-peptide is selected from 1-38, 1-40, and 1-42, and the nitrated forms thereof, and the term "Aβ-peptide" or "Aβ" is meant to include the Aβ-peptide selected from 1-38, 1-40, and 1-42, and the nitrated forms thereof, preferably Aβ-peptide 1-42. In one further preferred aspect of the method according to the present invention, said Aβ-peptide is a human Aβ-peptide.

Thus, further preferred is a method according to the present invention, wherein said region in said Aβ-peptide capable of being nitrated comprises a tyrosine at position 10 of said Aβ-peptide, and preferably is tyrosine at position 10 of said Aβ-peptide.

The amino acid sequence of the modified human Aβ-peptide according to the present invention reads: DAEFRHDSG<u>A</u>EVHHQKLVFFAEDVGSNKGAIIGLMVGGVVIA (SEQ ID NO. 2). This peptide comprises a mutation at the initial site for nitration at the tyrosine at position 10, which is replaced by an alanine (bold and underlined). Of course, other suitable amino acid replacements (i.e. other non-nitratable amino acids, such as phenylalanine) at this position are also encompassed by the term mutation according to the present invention. Another alternative is a chemically modified tyrosine, such as, for example, acetylation with Nacetylimidazole.

The amino acid sequence of the human Aβ-peptide reads: DAEFGHDSGFEVRHQKLVFFAEDVGSNK-GAIIGLMVGGVVIA (SEQ ID NO. 3). This peptide comprises three differences compared to the human Aβ-peptide, one of which is present at the initial site for nitration at the tyrosine at position 10 (differences in bold).

Certain methods of screening are known in the art and are discussed, e.g., in: In vitro Methods in Pharmaceutical Research, Academic Press, 1997; and in U.S. Pat. No. 5,030, 015. Preferred is a method for screening according to the present invention, wherein said potentially specific inhibitor is present in a compound library, a phage display library, in particular an sc-Fv phage display library, or in a library of antibodies. These libraries, their production and their screening in order to identify an inhibitor of the aggregation of amyloid-β peptide (Aβ) are known to the person of skill. Some libraries can be bought commercially and screened using machinery, such as robots.

The term "aggregation of amyloid-β peptide" shall mean the formation of aggregates of the amyloid-β peptide leading to plaques. Assays to determine the aggregation are described herein and well known from the respective literature, for example as cited herein.

Another aspect of the present invention then relates to the inhibitor screened according to the method according to the present invention. This inhibitor, according to the present invention, can be formulated into a pharmaceutical composition in a method for producing a pharmaceutical composition, comprising a method for identifying as above, and formulating said agent together with a pharmaceutically acceptable carrier, excipient, and/or stabilizer.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyl-dimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Preferred is a method according to the present invention, wherein said inhibitor is selected from a compound selected from small chemical molecules, peptides, and antibodies and fragments thereof, in particular a natural or recombinant Aβ-peptide lacking a region capable of being nitrated, such as an Aβ-peptide lacking a tyrosine at position 10 thereof, in particular a peptide selected from SEQ ID No. 2 or 3, and an antibody or fragment thereof that specifically binds to a region in said Aβ-peptide capable of being nitrated, in particular a 3NT10Aβ-antibody or fragment thereof, which can be selected from a monoclonal, polyclonal, human, humanized, and/or recombinant antibody or a functional fragment thereof, optionally comprising a label.

In the context of the present invention, a "region" in said Aβ-peptide capable of being nitrated shall be a part of the amino acid chain where a nitration, either enzymatically (e.g. through iNOS, nNOS, and/or eNOS) or chemically, can take place. Examples for amino acids that undergo nitration are cysteine, methionine, tryptophan, and tyrosine. Nitration reactions Preferably, said region is found around the tyrosine at position 10 of the human Aβ-peptide, and includes N- and C-terminally located amino acids (for example, if the region constitutes an epitope for an antibody), such as 1, 2, 3, 4, 5 or 6 N- and C-terminally located amino acids around the tyrosine (i.e. FRHDSG<u>Y</u>EVHHQ (SEQ ID NO. 4), SG<u>Y</u>EV, or G<u>Y</u>E in SEQ ID NO. 1). Furthermore, a region can also merely comprises the actual amino acid, that is, for example the tyrosine at position 10.

"Specifically binding" of the inhibitor shall mean that said substance exclusively or substantially exclusively binds and/or attaches to the region in said Aβ-peptide capable of being nitrated. Thus, incase of an antibody, said antibody shows no cross-reactivity or no substantial cross-reactivity with other antigens in the sample to be analyzed. One further example of specific binding is exclusive binding of, preferably, an antibody or functional fragment thereof, to the core of the Aβ-peptide plaque.

Preferred is a method according to the present invention, wherein said inhibitor inhibits the aggregation of said at least one Aβ-peptide through inhibiting nitration of said Aβ-peptide. That is, the formation of nitrated amino acids, such as 3'-nitrotyrosine is reduced or even completely inhibited. Another strategy is the inhibition of the aggregation of said at least one Aβ-peptide independently from the nitric oxide synthase (iNOS, nNOS, and/or eNOS) activity through blocking of the aggregation of the nitrated Aβ-peptide at the position of the nitration (preferably sterically). Yet another option would be the further chemical modification of the 3'-nitrotyrosine through the inhibitor, leading to a reduced or even completely inhibited aggregation.

Preferred is a method according to the present invention, wherein said method is performed in vivo in a recombinant non-human iNOS (−/−) mammal, in particular an APP iNOS (−/−) mouse, an APP (−/−) iNOS (−/−) mouse, or APP/PS-1 iNOS (−/−) mouse. The mouse is a convenient tool in order to further screen, identify and study prospective inhibitors of the aggregation of the at least one Aβ-peptide. In addition, modified Aβ-peptide (such as the natural mouse Aβ-peptide, and recombinantly modified human Aβ-peptides) and their effects independently of iNOS activity can be studied.

As mentioned above, a particularly preferred inhibitor according to the present invention is selected from antibodies and fragments thereof, in particular an antibody or fragment thereof that specifically binds to a region in said Aβ-peptide capable of being nitrated, in particular a 3NT10Aβ-antibody or fragment thereof, which can be selected from a monoclonal, polyclonal, human, humanized, and/or recombinant antibody or a functional fragment thereof, optionally comprising a label. Thus, the antibody or fragment thereof according to the present invention preferably has an immunoreactivity that is exclusively localized at the core of the Aβ-plaque.

Yet another important preferred aspect of the present invention then relates to a method for producing an antibody or fragment thereof that specifically binds to a region in an Aβ-peptide capable of being nitrated, in particular a 3NT10Aβ-antibody or fragment thereof, comprising the steps of a) affinity purification of a serum containing antibodies using a nitrated Aβ-peptide coupled to a chromatography column, or screening an sc-Fv phage display library using a nitrated Aβ-peptide, and b) optionally followed by a further purification step through exclusion of binding to at least one non-nitrated Aβ-peptide, such as a natural or recombinant Aβ-peptide lacking a tyrosine at position 10 thereof, such as the peptide according to SEQ ID No. 2 or 3. Respective details for these methods are known to the person of skill and as described herein, e.g. using a rabbit serum containing antibodies specific against a region in an Aβ-peptide capable of being nitrated, in particular a 3NT10Aβ-antibody or fragment thereof, for step a), or using natural or recombinant Aβ-peptides or parts thereof, such as a natural or recombinant Aβ-peptide lacking a tyrosine at position 10 thereof, such as the peptide according to SEQ ID No. 2 or 3 for step b).

Yet another important aspect of the present invention then relates to a pharmaceutical composition or formulation, produced according to a method according to the present invention as above containing the inhibitor as a diagnostic agent and/or therapeutic agent. Said pharmaceutical composition or formulation further contains a pharmaceutically acceptable carrier, excipient, and/or stabilizer. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyl-dimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Yet another important preferred aspect of the present invention then relates to a recombinant non-human iNOS (−/−) mammal, in particular an APP iNOS (−/−) mouse, an APP (−/−) iNOS (−/−) mouse, or APP/PS-1 iNOS (−/−) mouse. The mouse is a convenient tool in order to further screen, identify and study prospective inhibitors of the aggregation of the at least one Aβ-peptide. In addition, modified Aβ-peptide (such as the natural mouse Aβ-peptide, and recombinantly modified human Aβ-peptides) and their effects independently of iNOS activity can be studied. In this context yet another important preferred aspect of the present invention relates to a recombinant non-human APP (−/−) mammal, in particular an APP (−/−) iNOS (−/−) mouse, or APP (−/−)/PS-1 iNOS (−/−) mouse. Preferably, said mouse further expresses a recombinant APP having a tyrosine at position 10 of the Aβ-peptide. Preferably, said recombinant APP having a tyrosine at position 10 is a modified mouse APP (i.e. a partially humanized APP). Since the modification of the mouse APP at position 10 appears to be sufficient in order to lead to an aggregation of the Aβ-peptide (since mice do not develop Aβ-peptide plaques, even when the murine Aβ-peptide is overexpressed), the recombinant non-human APP (−/−) mammal represents an extremely useful animal model to further study the aggregation of the Aβ-peptide and disease progression.

Yet another important preferred aspect of the present invention then relates to a diagnostic method for determining the status and/or progression of the aggregation of amyloid-β peptide (Aβ) in a mammal, particularly a human patient, comprising the steps of a) detecting the amount and/or fraction of nitrated amyloid-β peptide in a sample obtained from a patient to be diagnosed using an antibody or fragment thereof that specifically binds to a region in an Aβ-peptide capable of being nitrated, in particular a 3NT10Aβ-antibody or fragment thereof, b) comparing said amount and/or fraction of nitrated amyloid-β peptide as detected with a control sample, and, optionally, c) concluding on the status and/or progression of the aggregation of amyloid-β peptide (Aβ) based on said difference in the amount and/or fraction as detected between the sample and the control sample.

The sample obtained from said mammalian patient to be diagnosed can be derived from any suitable sample, such as whole blood, serum, plasma, urine, lymph fluid, brain liquor, tissue samples, such as brain tissue samples and/or biopsies, and prepared tissue samples, such as histological slides.

In a preferred diagnostic method for determining the status and/or progression of the aggregation of amyloid-β peptide (Aβ) in a mammal, particularly a human patient, according to the present invention, said method further comprises the step of concluding on the status and/or progression of Alzheimers' disease based on said status and/or progression of the aggregation of amyloid-β peptide (Aβ) as determined. Said status and/or progression of the aggregation can be measures in accordance with test known in the state of the art, and can comprise determinations of the amount of plaques, the proportion of plaques formed by amyloid-β peptide 1-40 and/or amyloid-β peptide 1-42, the localization of said plaques in the brain, and can further include the determination of cognitive functions of said mammal, as it is known to the person of skill.

Yet another important preferred aspect of the present invention then relates to a diagnostic kit, comprising an inhibitor as identified according to the present invention and/or an antibody or fragment thereof according to the present invention, optionally together with additional auxiliary agents for performing a method according to the present invention as above. The kit preferably contains the chemical substances, dyes, buffers, and the like that are required to perform the methods according to the present invention. The kit can also contain protein chips or microarrays for the analysis, as well as manuals and software and machinery in order to display and interpret the results of the diagnosis.

Yet another important preferred aspect of the present invention then relates to an inhibitor as identified according to according to the present invention, an antibody or fragment thereof according to according to the present invention, an Aβ-peptide lacking a tyrosine at position 10 thereof, in particular a peptide selected from SEQ ID No. 2 or 3, or a pharmaceutical composition or formulation according to according to the present invention for use in the treatment of the aggregation of amyloid-β peptide (Aβ) and preferably Alzheimers' disease.

Another important preferred aspect of the present invention then relates to a method for treating synaptic dysfunction and oxidative stress resulting in neuronal degeneration in a patient in need thereof, comprising administering a therapeutically effective amount of an inhibitor as identified according to the present invention, an antibody or fragment thereof according to the present invention, an Aβ-peptide lacking a tyrosine at position 10 thereof, in particular a peptide selected from SEQ ID No. 2 or 3, or a pharmaceutical composition or formulation according to the present invention to said patient.

"Treatment" as used herein refers to both therapeutic treatment and prophylactic or preventative measures, wherein the object is to prevent or slow down (lessen) the targeted pathologic condition or disorder, in particular neuronal degeneration, aggregation of amyloid-β peptide (Aβ), and preferably Alzheimers' disease. Those in need of treatment include those already with the disorder as well as those prone to have the disorder or those in whom the disorder is to be prevented. The treatment can both include adjuvant treatments and first line treatments of treatment-naive patients, and can be combined with other anti neuronal degeneration strategies, such as chemotherapies. Preferably, said treatment in said patient is for the treatment of Alzheimers' disease.

Another important preferred aspect of the present invention then relates to a method for improving cognitive functions in a patient suffering from neuronal degeneration, in particular from Alzheimers' disease, comprising administering a therapeutically effective amount of an inhibitor as identified according to the present invention, an antibody or fragment thereof according to the present invention, an Aβ-peptide lacking a tyrosine at position 10 thereof, in particular a peptide selected from SEQ ID No. 2 or 3, or a pharmaceutical composition or formulation according to the present invention to said patient.

The inducible form of the nitric oxide synthase (iNOS), is transcriptionally upregulated in Alzheimer's disease. In the context of the present invention, the inventors determined the effect of iNOS deficiency in amyloid precursor protein/presenilin 1 (APP/PS1) transgenic mice. APP/PS1/iNOS (−/−) mice as well as APP/PS1 mice treated with the iNOS specific inhibitor L-NIL showed a significant reduction of working memory errors in the radial arm maze-test at 3 and 12 months of age as well as improvement of LTP at 3 months of age. Furthermore, APP/PS1/iNOS(−/−) mice revealed decreased amyloid β (Aβ) burden at 12 months, as detected by thioflavin S. Aβ 1-40 and 1-42 levels in brain extracts of these mice were reduced. This reduction could not be attributed to reduced microglial phagocytosis of Aβ. Instead, the inventors observed a decrease in the activity of insulin degrading enzyme (IDE) in APP/PS1 mice, which was rescued by iNOS gene deletion. IDE activity, in contrast to neprilysin, was also found to be specifically inhibited by nitric oxide in vitro. More importantly, the inventors observed that nitration of Aβ at tyrosine 10 strongly induces its aggregation. Raising a specific antibody against the Aβ(3NT-Y10) epitope the inventors were able to detect nitrated Aβ in plaques of APP/PS1 mice.

These results suggest that iNOS expression aggravates AD-like neuropathological changes, starting early with electrophysiological and behavioral phenotypes and ending with increased aggregation and decreased degradation of Aβ by IDE.

The invention shall now be further described in the following examples with reference to the accompanying Figures, nevertheless, without being limited thereto. For the purposes of the present invention, all references as cited herein are incorporated by reference in their entireties.

FIGS. 1A-1E shows (1A) Working memory errors (left panel) and reference memory errors (1B) (right panel) of radial arm maze test at 3 month of age of wild type, APP/PS1, APP/PS1 iNOS (−/−), and APP/PS1 animals treated with L-NIL from 2-3 month of age (n=15±SEM, one-way ANOVA, Student-Newman-Keuls post test, ***p<0.001 (1C) RIPA and SDS brain extracts of 5 month old APP/PS1 and APP/PS1 iNOS (−/−) were separated by 4-12% NuPAGE and immunoblotted using antibodies against APP, APP-CTFs, Aβ, IDE, Neprilysin, PS1 and tubulin (1D) Densitometric quantification of insoluble Aβ from C (n=4+/−SEM) (1E) Quantification of soluble (RIPA) and insoluble (SDS) Aβ1-40 and 1-42 from 5 month old APP/PS1, APP/PS1 iNOS (−/−), and APP/PS1 animals treated with L-NIL from 2-3 month of age mice by sandwich ELISA. (n=6±SEM).

FIGS. 2A-2E shows (2A) Determination of the amplitude of the mean field excitatory postsynaptic potential (fEPSP) in the Schaffer collateral of wild type, APP/PS1, iNOS (−/−); APP/PS1, iNOS (−/−) and APP/PS1 mice treated with the selective iNOS inhibitor L-NIL from 2-3 month as percent of baseline. (n=5+/−SEM) Right panel: Evaluation of the early (slope 1; 10 min after LTP induction) and late LTP phase (slope 2; 50 min after LTP induction) of the amplitude of the mean fEPSP (n=5+/−SEM of ten minutes recordings, one-way ANOVA, Newman-Keuls post test, *p<0.05; p<0.01; *p<0.001) (2B) Determination of the slope of the mean fEPSP as in A. Right panel: Evaluation of the amplitude of the mean fEPSP (2C) Immunblot of brain homogenates and synaptosomal fractions in wild type and APP/PS1 animals at 12 month of age using an anti-S-nitrocystein specific antibody. (2D) Coomassie stain of anti-S-nitrocystein antibody precipitated synaptosomal fractions from wild type, APP/PS1, APP/PS1 iNOS (−/−) and APP/PS1 L-NIL mice separated by SDS-PAGE (2E) Protein sequence of Hsp75/mortalin. Underlined sequences were recovered after tryptic digestion by mass spectrometry (2F) Synaptosomal fractions of wild type, APP/PS1, and APP/PS1 iNOS (−/−) mice were immunoprecipitated using an antibody against Hsp75, separated by SDS-PAGE and immunoblotted using an antibody against Grp94.

FIGS. 3A-3G shows (3A) Working memory errors (left panel) and reference memory errors (right panel) of radial arm maze test at 12 month of age of wild type, APP/PS1, APP/PS1 iNOS (−/−), and APP/PS1 animals treated with L-NIL from 6-12 month of age (mean±SEM, n=15, ANOVA followed by Student-Newman-Keuls test, *p<0.05; p<0.01; *p<0.001). (3B) RIPA and SDS brain extracts of 12 month old APP/PS1 and APP/PS1 iNOS (−/−) were separated by 4-12% NuPAGE and immunoblotted using antibodies against APP, APP-CTFs, Aβ, IDE, Neprilysin, PS1 and tubulin (3C) Densitometric quantification of insoluble Aβ from C (n=4+/−SEM) (3D) Quantification of soluble (RIPA) and insoluble (SDS) Aβ1-40 and 1-42 from 12 month old APP/PS1, APP/PS1 iNOS (−/−) by sandwich ELISA. (n=5±SEM) (3E) Quantification of soluble (RIPA) and insoluble (SDS) Aβ1-40 and 1-42 from 12 month old APP/PS1 and APP/PS1 animals treated with L-NIL from 6-12 month of age by sandwich ELISA. (n=5±SEM) (3F) Thioflavin S histochemistry of APP/PS1 and APP/PS1 iNOS (−/−) mice at 12 months of age showing Aβ deposits within the hippocampus (Hc) and the neocortex (Cx). (3G) Evaluation of 15 consecutive sections per animal (n=12±SEM, Student's t-test, ***p<0.001).

FIGS. 4A-4D shows that NO does not regulate microglial Aβ phagocytosis in vitro or in vivo. (4A) Analysis of phagocytosis of primary microglia cells from wild type (wt) and iNOS deficient (iNOS (−/−)) mice exposed to 500 nM fibrillar FAM labeled Aβ1-42 peptide for up to 6 h. (4B) Primary microglial cells treated with the iNOS inhibitor L-NIL (10 μM) or the NO donor SNAP (100 μM) did not expose differences in Aβ1-42 phagocytosis. (4C) Immunohistological colocalization analysis of Aβ and the microglial marker CD11b in 12 month old APP/PS1 and APP/PS1 iNOS (−/−) mice by confocal microscopy using antibodies 6E10 and MCA711, respectively. (4D) Statistical analysis of 15 consecutive sections (n=12±SEM).

FIGS. 5A-5E shows (5A) Activity of recombinant IDE was monitored using a fluorgenic peptide substrate. (5B) IDE was preincubated for 30 min with different concentrations of Sin-1. Fluorescence was measured for up to 2 h in 3 minute intervals (n=2+/−SEM of a representative experiment out of three) (5C) Recombinant IDE (50 ng) was incubated with the NO donor Sin-1 for 4 h. Samples were separated by 4-12% NuPAGE and IDE was detected by immunoblot using antibody PC730, whereas nitrated IDE was detected using 3-nitrotyrosine specific anti-body 1A6 (5D) Recombinant IDE (60 ng) was 1 h preincubated with increasing concentrations of Sin-1 for 1 h, followed by the addition of 140 ng Aβ1-42 and incubation for 2 h at 37° C. Samples were separated by 4-12% NuPAGE and immunoblotted using antibodies PC720 against IDE and 6E10 against Aβ (5E) RIPA fractions of 12 month wild type, APP/PS1 and APP/PS1 iNOS (−/−) animals were monitored for their ability to cleave a fluorgenic peptide substrate in the presence of the neprilysin inhibitor phosphoramidon (n=4+/−SEM, one way anova followed by Tukey post hoc test, **p>0.01, *p<0.05)

FIGS. 6A-6D shows (6A) Synthetic Aβ1-42 or Aβ1-42Y10A were incubated with buffer, Sin-1 or PN for 18 h and afterwards separated by SDS-PAGE and immunoblotted using anti-body 6E10. (6B) Same assay as in A but samples were incubated for different time periods with PN. The resulting high molecular aggregates (>40 kDa) were densiometrically quantified (n=2+/−SEM) (6C) Synthetic Aβ1-42 or (6D) Aβ1-42Y10A were incubated with buffer, Sin-1 or PN for 18 h and afterwards analyzed by MALDI-TOF.

FIGS. 7A-7F shows (7A) Synthetic Aβ1-42 peptide or Aβ1-42Y10A were treated in the absence and presence of PN and immediately separated by SDS-PAGE. After immunoblotting 3NT-Aβ was detected using the anti 3NT-Aβ serum. The blot was reprobed using antibody 6E10. (7B) Confocal sections of a 12 month old APP/PS1 mouse stained with antibody IC16 for Aβ and anti 3NT-Aβ serum. 3NT-Aβ was exclusively found in the core of Aβ plaques. Bar=20 μm. (7C) High magnification confocal pictures of a plaque of 12 month old (upper panel) and a 18 month old (lower panel) animal. Bar=10 μm. (7D) Confocal 3D reconstruction of an Aβ plaque of a 12 month old APP/PS1 mouse stained with antibody IC16 for Aβ and anti 3NTAβ serum. Bar=10 μm. (7E) 7PA2 cells and CHO cells were stained using the purified anti 3NT-Aβ serum according to the present invention. (Bar=10 μM). F) 3NT-Aβ was measured by sandwich ELISA in wild type, APP/PS1 and APP/PS1 iNOS (−/−) mice at 12 month of age (n=4+/−SEM, Students t-test, **p<0.01).

FIGS. 8A-8E shows the induction of β-amyloidosis by 3N Tyr$^{10}$-Aβ (8A) 25 μM Aβ$_{1-42}$ were incubated for 5 h with increasing amounts of either peroxynitrite (Aβ42PN) treated or synthetically nitrated Aβ$_{1-42}$ (Aβ42(3NT)Y) and oligomeric forms were detected using antibody IC16 (8B) Determination of the nitration and aggregation status of Aβ$_{1-42}$ used for intracerebral injection by Western blot using 3N Tyr$^{10}$-Aβ (left panel) and 6E10 (right panel). (8C) Aβ$_{1-42}$ and (8D) nitrated Aβ$_{1-42}$ were intracerebrally injected into APP/PS1 mice. Sections were analyzed 8 weeks later using antibodies IC16, 3NTyr$^{10}$-Aβ and Iba1, and by thioflavin S. Bar=200 μM, lower panel bar=50 μm (8E) Enlargement of a newly seeded plaque from B. Bar=2 μM.

Figure 9A:
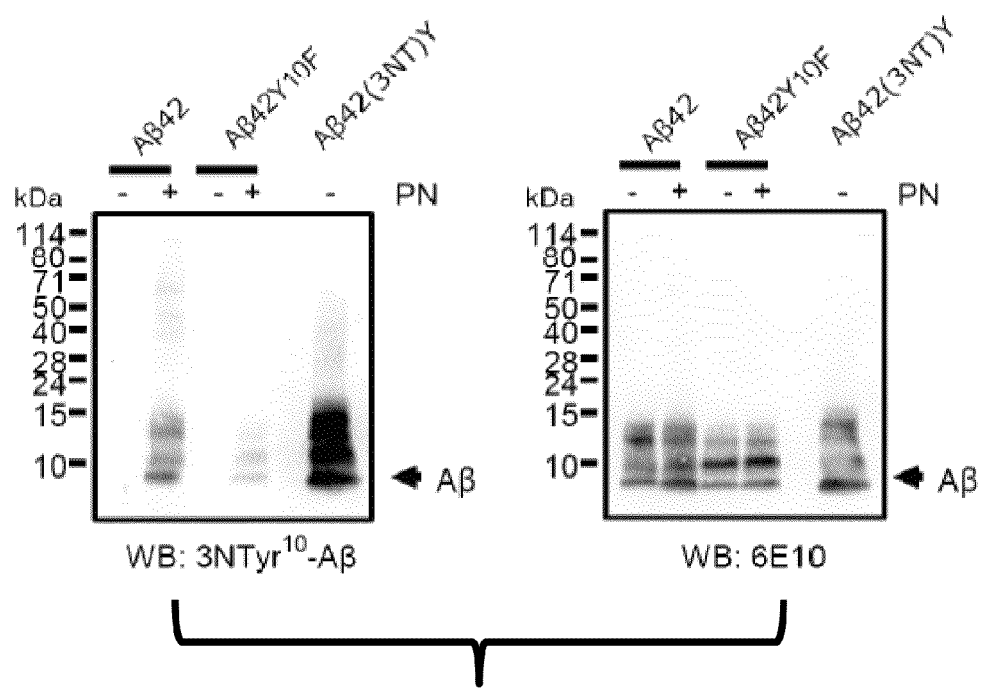
Figure 9B:
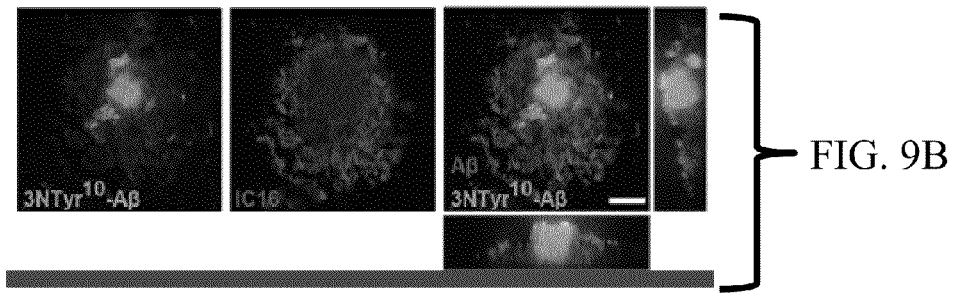
Figure 9C:
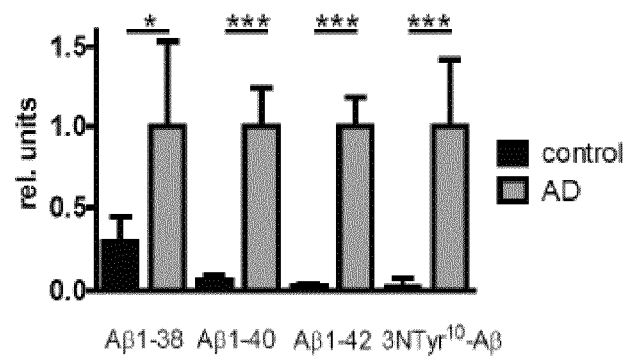

FIGS. 9A-9C shows the detection of Aβ nitrated at tyrosine 10 in AD brains (9A) Detection of Aβ1-42 (Aβ42), Aβ1-42Y10F (Aβ42Y10F) both with and without incubation with 0.25 mM peroxynitrite and synthetically nitrated Aβ1-42 (Aβ42(3NT)Y) using 3NTyr10-Aβ antiserum and reprobing with 6E10 (9B) Immunhistochemical detection of nitrated Aβ in human AD tissue using IC16 against Aβ and 3NTyr10-Aβ aniserum by confocal microscopy (bar=20 μm) (9C) Relative quantification of Aβ1-38, 1-40, 1-42 and 3NTyr$^{10}$-Aβ in the SDS fraction of AD brains and controls measured by ELISA. (n=5 for control and n=8 for AD+/−SEM, Students t-test, *p<0.05, ***p<0.001).

FIGS. 10A-10D shows that the nitration of Aβ at tyrosine 10 induces its aggregation (10A) Aggregation of synthetic Aβ$_{1-42}$ (Aβ42), nitrated Aβ$_{1-42}$ (Aβ42+PN), and nitrated Aβ$_{1-42}$Y10F (Aβ42Y10F+PN) was analyzed by Western blot using antibody 6E10 (10B) Reprobing with 3NTyr$^{10}$-Aβ antiserum to detect Aβ nitration (10C) Graphical evalution of three independent experiments normalized to Aβ monomer (n=3+/−SEM, two-way ANOVA, Bonferroni post test, ***p<0.001) (10D) Thioflavin T aggregation assay of synthetic Aβ$_{1-42}$ (Aβ42), nitrated Aβ$_{1-42}$ (Aβ42+PN), and nitrated Aβ$_{1-42}$Y10F (n=3+/−SEM, two-way ANOVA Aβ42 vs. Aβ42+PN, Bonferroni post test, *p<0.05).

SEQ ID No. 1 shows the amino acid sequence of human Aβ1-42 peptide.

SEQ ID No. 2 shows the amino acid sequence of human Aβ1-42Y 10A peptide.

SEQ ID No. 3 shows the amino acid sequence of mouse Aβ1-42 peptide; and

SEQ ID NO. 4 shows the amino acid sequence of the region around T10 in human Aβ1-42 peptide.

SEQ ID NO. 5 shows the amino acid sequence of a mutated region around T10 in human Aβ1-42 peptide.

EXAMPLES

In the context of the present invention, the inventors determined the effect of iNOS deficiency in amyloid precursor protein/presenilin1 (APP/PS1) transgenic mice on spatial memory, hippocampal long term potentiation (LTP), amyloid pathology and neuroinflammation.

Material and Methods
Abbreviations

L-NIL, L-N6-(1-iminoethyl)-lysine; AEBSF, 4-(2-amino ethyl)benzenesulfonyl fluoride hydrochloride; PN, peroxynitrate; Sin-1,3-morpholino-sydnonimine; L-NIL, L-N6-(1-Iminoethyl)lysine Animals APP/PS1 transgenic animals expressing the mouse APP containing the human amyloid β domain as well as the Swedish mutation and the presenilin 1 Δ exon 9-mutation both under the control of the prion promoter (#004462, The Jackson Laboratory)[18] and iNOS deficient animals resulting from disruption of exons 12 and 13 of the iNOS gene (#002609, The Jackson Laboratory)[19] were both of the BC57/B16 genetic background. L-NIL was given orally in the water either from 2-3 month or from 6-12 month of age. The drug was replaced daily because of the short half live of L-NIL. Mice were housed in groups of 4 under standard conditions at 22° C. and a 12 h light-dark cycle with free access to food and water. At the time of sacrifice animals were anaesthetized, transcardially perfused with heparinized sodium chloride (0.9%), and brains were removed. Animal care and handling was performed according to the declaration of Helsinki and approved by the local ethical committees.

Radial Arm Maze

Eight arm radial maze. Learning and memory testing for each mouse were conducted in an eight arm maze constructed of wood and elevated 50 cm from the floor. Each of the arms was 60 cm long and 6 cm wide and extended from an octagonal central platform 10 cm across. Food cups 1 cm deep were placed 2 cm from the end of each arm. The testing room contained several visual cues outside of the maze and was lit dimly while sessions were in progress. Initially, the mice were trained for 3 d. During each training session the mouse was placed on the center platform and allowed to move freely in the maze to obtain food pellets, which were presented in all eight arms, for a period of 10 min. From day 4 on the mice were tested one session per day for a total of 14 d. During the test sessions four randomly selected arms were baited with one pellet of food each; the baited arms were kept unchanged throughout the experiment. The mouse was allowed to move freely in the maze until it collected the four pellets of food or until 10 min passed, whichever occurred first. Parameters evaluated were: (1) reentry into baited arms that had been visited during the session (working memory error), and (2) entries into unbaited arms (reference memory error). The task was considered learned when the working memory error was zero and the average reference memory error was one or less than one in three successive sessions[20].

Primary Microglial Cell Culture

Primary microglial cell cultures were prepared as previously described. Briefly, mixed glial cultures were prepared from newborn mice and cultured in DMEM supplemented with 10% FCS and 100 U ml$^{-1}$ penicillin/streptomycin. After 10-14 days of primary cultivation, microglial cells were harvested by shake off.

Brain Protein Extraction

Snap-frozen brain hemispheres were homogenized in PBS with protease inhibitor mixture (Sigma, Munich, Germany). In case of the enzymatic assays the protease inhibitor mixture was replaced with 1 mM AEBSF. The homogenate was extracted in 25 mM Tris-HCl pH 7.5, 150 mM NaCl, 0.5% sodium deoxycholate, 1% NP-40 for 30 min on ice. After centrifugation at 100000×g for 30 min at 4° C. the resulting supernatant containing the soluble proteins was saved and the pellet was sonified in 25 mM Tris HCl pH 7.5, 2% SDS resulting in the solubilization of insoluble proteins. Protein concentration in the soluble fraction was determined using the BCA protein assay (Thermo, Bonn, Germany). Protein samples (25 µg) were separated by 4-12% NuPAGE (Invitrogen, Karlsruhe, Germany) using MES or MOPS buffer and transferred to nitrocellulose membranes. For detection of Aβ, blots were boiled for 5 min in water. Aβ was detected using antibody 6E10 (1:2000; Covance), APP and CTF using antibody 140 (1:2500; (Wahle), IDE using antibody PC730 (1:5000; Calbiochem), neprilysin using antibody 56C6 (1:1000; Santa Cruz), presenilin using antibody PS1-NT (1:1000; Calbiochem), and tubulin using antibody E7 (1:5000; Developmental Studies Hybridoma Bank) as a loading control, followed by incubation with appropriate horseradish peroxidaseconjugated secondary antibodies. Immunoreactivity was detected by enhanced chemiluminescence reaction (Millipore, Schwalbach) and luminescence intensities were analyzed using Chemidoc XRS documentation system (Biorad, München, Germany).

Aβ Elisa

Quantitative determination of $A\beta_{1-40}$ and $A\beta_{1-42}$ was performed using the human amyloid $A\beta_{1-40}$ and $A\beta_{1-42}$ ELISA kits (The Genetics Company, Switzerland) according to the manufacturer's protocol. Samples were cleared by centrifugation at 100,000×g for 20 min and diluted to meet the concentration range of the standard curve.

Synaptosomal Preparation

In brief, APP/PS1, iNOS (−/−), APP/PS1, and WT animals were decapitated, their brains explantated, weighted and homogenized in 9× volume of 5 mM NaF, 2 mM NaVa, 5 mM pyrophosphate, 1 mM PMSF, 1 mM EDTA, 0.1 mM Tris acetate 0.32M sucrose (10% w/v) including protease inhibitor cocktail (Sigma-Aldrich, Steinheim, Germany), using a drill-driven pestle (15 pulses at 700×rpm). 2 ml of the homogenate were then centrifuged at 800×g for 5 minutes at 4° C. Approximately 1.200 µl of supernatant (crude fraction) were obtained of which 600 µl were pelleted at 16,000×g for 20 minutes at 4° C. The pellet was resuspended in 300 µl of 0.32 M sucrose buffer (homogenization buffer; washed fraction). A gradient of homogenization buffers with ascending sucrose concentrations (300 µl 1.4 M sucrose and 500 µl 1.0 M sucrose) was centrifuged for 10 minutes at 9100×g. and 4° C. The lower interphase (130-160 µl) was collected and 2 vol. water containing 1:500 PIC were added. Synaptosomes were pelleted for 20 minutes at 16,000×g and 4° C. For subsequent polyacrylamidegelelectrophoresis, the pellet was extracted in 50-150 µl of RIPA buffer for 20 minutes at 4° C. For immunoprecipitation of nitrosylated proteins 0.5 µg of anti-5-nitrosocysteine (Sigma-Aldrich, Steinheim, Germany) antibody were mixed with 50 µl protein G sepharose (Sigma-Aldrich, Steinheim, Germany) incubated over night at 4° C. on a rotator. The sepharose beads were washed twice with 500 µl ice-cold RIPA buffer before use and added to 500 µg total protein of synaptosomal lysates and incubated over night at 4° C. on a rotator. Beads were washed twice with RIPA and afterwards incubated at 20° C. with 40 µl of 1× NuPage LDS sample buffer without any reducing agent to prevent denitrosylation. Samples were loaded on 4-12% Bis-Tris NuPage gels and separated at 120 V in MOPS buffer (Invitrogen, Karlsruhe, Germany). The gel was fixed for 1 hour at room temperature in 50% ethanol, 3% phosphoric acid in water, washed 3× for 20 minutes in water, incubated for 1 hour in 34% methanol, 3% phosphoric acid, 17% ammonium sulfate in water (staining solution) and then stained over night at 4° C. in staining solution containing 0.53 g Coomassie G250 per 1.5 l. Gels were washed 3× for 20 minutes in water and the bands of interest were cut out, using a new singleuse scalpel. The bands obtained were stored at −80° C. until Maldi-TOF analysis.

Phagocytosis of Aβ

Microglial phagocytosis of FAM-labeled $A\beta_{1-42}$ (FAM-Aβ) (Anaspec, San Diego, Calif.) was measured by plate based assay. Cells were plated at 50000 cells per well. After 1 h cells Aβ was added to a final concentration of 500 nM and incubated. Finally, the Aβ-containing medium was removed and extracellular Aβ was quenched with 100 µl 0.2% trypan blue in PBS pH 4.4 for 1 min. After aspiration fluorescence was measured at 485 nm excitation/535 nm emission using a Spectrafluor Plus reader (Tecan, Austria). To normalize for cell numbers 100 μl 50 μg/ml H33342 in PBS was added, incubated for 30 min and the fluorescence measured at 360 nm excitation/465 nm emission.

Histology

Serial sagittal sections (10 μm) were cut from cryo-conserved preserved hemispheres (Leica Cryostat CM 3050S), embedded in tissue freezing medium (Jung/Leica Microsystems, Nussloch, Germany) and mounted (Microscope Slides #K0123b, Engelbrecht, Germany). After drying slides were fixed in 4% paraformaldehyde (Roti Histofix, Roth, Karlsruhe, Germany) for 20 min and blocked in 5% serum for one hour. Between the steps, slides were rinsed three times for five minutes in PBST. Immunostaining was performed overnight at 4° C. using primary antibodies: 1.) polyclonal antibody rabbit-anti-glial fibrillary acidic protein (1:900 in 2% normal donkey serum in PBST; DAKO Z0334, Glostrup, Denmark). 2.) monoclonal anti-body mouse-anti-neuronal nuclei (1:250 in 2% normal donkey serum in PBST; Serotec MCA341G, Dusseldorf, Germany). Afterwards slides were incubated with Alexa Fluor 594-labeled secondary antibodies hosted in goat for one hour (1:400 in PBST; Invitrogen #A11037 & #A11020 Karlsruhe, Germany). For co-staining with Hoechst Dye 33342 (10 μg/ml; Fluka, Steinheim, Germany) an incubation time of two minutes was set. Again, slides were rinsed with PBST between the steps. Finally, the slides were covered in Mowiol 4-88 (Calbiochem/VWR #475904, Darmstadt, Germany) and stored at −20° C. in the dark until microscopy was performed. Alternatively, brains were fixed in 4% paraformaldehyde for 18 h, washed in 70% ethanol for 2 h and stored in PBS afterwards. Brain hemispheres were sectioned saggitally using a vibratome (Leica, Wetzlar, Germany). Antigen retrieval was performed by heating sections at 80° C. in 100 mM citric acid pH 6. Sections were stained free floating using anti-bodies 1C16 against Aβ (Lit), an antibody against CD68, and Abl-93 against lamp2. Thioflavin S staining was performed on cryosections dried for 30 minutes at room temperature and fixed in 4% paraformaldehyde (Histofix, Roth, Karlsruhe, Germany) for 20 minutes. Slices were rinsed 3 times in distilled water and incubated in 0.01% thioflavin S in 80% ethanol and afterwards differentiated in 80% ethanol for 35 minutes. Samples were dried for 10 minutes, mounted in Mowiol 4-88 (Calbiochem, Darmstadt, Germany).

In vitro Electrophysiology

Physiological recordings were performed on brain slices from 3 month old male and female mice, obtained after anesthetization with isoflurane and decapitation. The brain was immediately dissected and sagitally sliced in 400 μm sections using a vibratome (Camden Instruments, Integraslice 7550 PSDS). Hippocampi were isolated and transferred into an interface chamber at 29° C. in an oxygen-enriched atmosphere in artificial cerebrospinal fluid (aCSF) containing 124 mM NaCl, 4 mM KCl, 1.24 mM $NaH_2PO_4$, 1.3 mM $MgSO_4$, 26 mM $NaHCO_3$, 10 mM D-glucose, and 1 mM $CaCl_2$. After 30 min of recovery the $CaCl_2$ concentration was increased to 2 mM and incubated for 30 min. Finally, slices were moved to an interface recording chamber were they equilibrated for another 15 min. The stimulating electrode was placed in the cornu ammonis 2 (CA2) region of the Schaffer collaterals and the recording electrode in the CA1 region of the pyramidal cell layer. The recording of the field excitory postsynaptic potential (fEPSP) was imitated after 15 min of basal recording. Basal synaptic transmission (BST) was assessed by plotting the current (mA) against the peak amplitudes of fEPSP to generate input-output relations. Paired pulse facilitation (PPF) were recorded by applying interstimulus intervals of 30, 50, 75 and 100 ms. For long term potentiation (LTP) experiments a 15 min baseline were recorded with a interpulse interval of one minute at an intensity that evoked a response approximately 30% of maximum fEPSP. The LTP was induced by a thetaburst consisting of 4 trains of 10 pulses at 100 Hz separated by 200 ms.

Coimmunoprecipitation of Hsp75

0.5 μg of anti-Hsp75 antibody (clone 30A5, GenTex, San Antonio, Tex., U.S.A.) was preincubated with protein G sepharose and incubated with 330 μg total protein of purified synaptosomes. Pellets were washed and incubated at 70° C. on a thermostat at 350 rpm for 10 minutes with 40 μl of 1× NuPage LDS sample buffer containing 80 mM DTT, transferred for 1 hour on 0.45 μm PVDF membrane. GRP94 was detected using antibody ab13509 (abcam, Cambridge, Mass., U.S.A.) at a 1:500 dilution in TBST 0.02% NaF after blocking with 0.3% Tween in TBST. Bands were detected using ECL (Millipore, Schwalbach, Germany) and quantified using the molecular imager ChemiDoc XRS system (Bio-Rad, München, Germany).

Enzymatic Assays

Fluorogenic Substrate V (7-methoxycoumarin-4-yl) acetyl-RPPGFSAFK-2,4-dinitrophenyl; R&D) a substrate for IDE and neprilysin, was used to monitor the effect of the nitric oxide releaser Sin-1 (Cayman). For that 20 ng recombinant IDE (R&D) in 100 mM Tris pH 7.5, 1 M NaCl or 50 ng recombinant neprilysin (R&D) in 100 mM Tris pH 7, 150 mM NaCl were preincubated for 30 min with different concentration of Sin-1. Afterwards the substrate was added to a final concentration of 10 μM. The hydrolysis of substrate V was measured based on the increase of fluorescence (exitation 320 nm/emission 405 nm) using a Spectrafluor Plus (Tecan, Austria) plate reader for a time period of up to 60 min in 1 min intervals at 37 C. Determination of IDE activity in mouse brain was performed using the fluorogenic peptide substrate 2-aminobenzoyl-GGFLRKHGQ-ethylenediamine-2,4-dinitrophenyl (Bachem, Switzerland)[21]. For that mice brains were homogenized in PBS containing 1 mM AEBSF, extracted with 1% Tx-100 and centrifuged at 100000×g for 30 min. 10 μg of supernatants were incubated with 25 μM phosphoramidon to inhibit endogenous neprilysin activity. The fluorogenic substrate was added to a final concentration of 20 μM and the resulting fluorescence signal was measured (excitation 320 nm/emission 413 nm) every 3 min for up to 2 h at 37° C. using a infinite 200 plate reader (Tecan, Austria). Evaluation was done within the linear range of the reaction.

Aβ Degradation Assay

To determine the effect of Sin-1 on the degradation of Aβ 160 ng Aβ1-42 (Sigma, Munich, Germany were incubated with 60 ng recombinant IDE (R&D) in the presence of indicated concentrations of Sin-1 in 100 mM Tris pH 7, 150 mM NaCl for 2 h at 37 C. Samples were separated by 4-12% Nupage and immunoblotted. Aβ was detected using antibody 6E10 and IDE was detected using antibody PC730 (Calbiochem, San Diego, Calif.) against IDE.

Aβ Aggregation Assay

Amyloid β 1-42 or Amyloid β 1-42 Y10A (both from rPeptide, Bogart, Ga., USA) were incubated with either 5 mM Sin-1 or 0.25 mM peroxynitrite in PBS for 18 h at 20° C. Peptides were separated by 4-12% Nupage and blotted transferred nitrocelluse and incubated with antibody 6E10 (Signet). The remaining sample was stored at −20° C. and analyzed by mass spectrometry. In case of the time course experiment the reaction was stopped using Nupage sample buffer followed by incubation at 70 C for 5 min.

Aβ1-42, Aβ1-42 Y10F (Peptide Specialty Laboratories) were solubilized as previously described. For nitration samples were incubated with 0.25-0.5 mM peroxynitrate in water while vortexing. Aggregation was started by diluting samples to 25 μM using 50 mM Tris-HCl pH 7. Samples were separated by 4-12% NuPAGE and aggregates were detected using anti-body 6E10 (Signet) and 3-NTyr10-Aβ. Aggregation was expressed as a ratio between the signal above 30 kDa and the Aβ monomer, normalized to the 0 time point of Aβ1-42. Thioflavin T fluorescence assays were performed as described previously. Fluorescence was read at 446 nm (excitation) and 482 nm (emission) using a fluorescence spectrophotometer (Varian).

3'-Nitrotyrosine Specific Amyloid β Antibody

The antibody recognizing the 3-nitrotyrosine 10 of Aβ was generated by rabbit immunization using the synthetically nitrated peptide FRHDSG(3NT-Y)EVHHQ (SEQ ID No. 4) Eurogentech, Liege, Belgium). The resulting serum was first immunopurified against the nitrated peptide. In a second purification step antibodies with reactivity against the unmodified peptide were removed by immunochromatography against the peptide FRHDSGEVHHQ (SEQ ID No. 5). Cryotome brain sections of APP/PS1-transgenic mice at plaque age were fixed for 5 min in 4% paraformaldehyde and stained with anti-3NT-Aβ serum (1:200) and mouse anti-body IC16 recognizing human Aβ1-17 (1:200). Sections were analyzed using a BX61 microscope equipped with an disk scanning unit to achieve confocality (Olympus, Hamburg, Germany). Pictures were additionally deconvoluted with Cell^P (Olympusm, Hamburg, Germany) using the nearest neighbor method.

ELISA for 3NT-Aβ

High binding clear 96 well plates were coated with 50 μl 20 μg/ml3NT-Aβ antibody in PBS 4 h at 20° C. Plates were blocked with 100 μl 3% BSA in TBS for 15 min. 10 μl of 2% SDS fractions from mouse brain were diluted with 50 μl 6.5% Tx-100, 25 mM Tris-HCl pH 7.5, 150 mM NaCl. 50 μl Samples were incubated for 18 h at 4° C., washed 5 times with TBST and incubated with 50 μl 6E10 diluted 1:10000 in TBST for 2 h at 20° C. Wells were washed 5 times with TBST and 50 μl goat anti mouse-HRP diluted 1:10000 with TBST was added and incubated for 2 h at 20° C. Finally, the wells were washed 5 times with TBST and 50 μl TMB ultra substrate (Thermo, Bonn, Germany) was added. The reaction was stopped after 20 minutes using 2M sulphuric acid. Absorption at was determined at 450 nm within 15 min using a infinite 200 plate reader (Tecan, Austria).

Intracerebral Injections 2.5 month old APP/PS1 mice (n=3) were anesthetized with ketamine (30 mg/kg) and xylazine (4 mg/kg). 2.5 μl of 0.25 mg/ml Aβ solutions were injected intra-cortically into the right hemisphere anteroposterior−2.5, lateral 2.0 at 1.0 mm (cortex) and in addition at 1.5 mm (hippocampus) depth relative to the bregma at a rate of 1 μl/min. Control solutions were injected into the left hemisphere, accordingly. Mice were sacrificed 8 weeks later. Cryosections in the proximity of the injection channel were stained using antibodies IC16, 3NTyr10-Aβ and anti-Iba1 (1:400, Wako). References 1. Heneka, M. T. et al. Neuronal and glial coexpression of argininosuccinate synthetase and inducible nitric oxide synthase in Alzheimer disease. J. Neuropathol. Exp. Neurol. 60, 906-916 (2001). 2. Vodovotz, Y. et al. Inducible nitric oxide synthase in tangle-bearing neurons of patients with Alzheimer's disease. J. Exp. Med. 184, 1425-1433 (1996).

Human Samples.

Human brain samples were from the parietal cortex of 5 age control and 8 diagnosed AD patients (Braak staging V-VI, CERAD B-C). The post mortem interval (PMI) was comparable among groups ranging from 4-48 h. Samples were extracted as the mouse brains described above with the exception that instead of RIPA buffer 25 mM Tris-HCl pH 7.5, 150 mM NaCl, 1% Tx-100 was used. CSF samples were from 10 control, 10 mild cognitive impaired and 10 diagnosed AD patients.

Results

APP/PS1 iNOS (−/−) mice showed a reduction in working and reference memory errors at 3 and 12 month of age, whereas a decrease in Aβ deposition was only detectable at 12 month of age. In addition, the inventors could observe a reduction in working and reference memory errors in APP/PS1 mice treated with the iNOS selective inhibitor L-NIL. Since APP processing was found to be unaffected by iNOS gene deficiency, the inventors concluded that increased degradation of Aβ might account for the reduction in Aβ deposition. Activity assays demonstrated an inhibitory effect of NO on IDE activity, but not for neprilysin. In contrast, neither microglial phagocytosis nor Aβ aggregation were modulated by NO. Importantly, assessment of hippocampal LTP showed that the APP/PS1 expression induced LTP suppression was completely prevented by either iNOS gene deficiency or L-NIL treatment. Analysis of synaptosomal preparations demonstrated iNOS-dependent nitroyslation of the chaperone GRP75.

Behavioral Phenotyping in Preplaque APP/PS1 Mice

Since impaired short term memory has been demonstrated in Alzheimer's disease mouse models[22,23] the inventors tested iNOS deficient mice on memory deficits in the APP/PS1 model. In addition, the inventors preventively treated mice with the iNOS specific inhibitor L-N6-(1-iminoethyl)-lysine (L-NIL) from 2 to 3 month of age. To exclude motor impairments the inventors performed open field tests one week before the radial arm maze tests. Analysis of motor activity did not show differences among the different groups (see supplementary FIG. 1). Radial arm maze tests at 3 month of age revealed a reduction of reference and working memory errors of APP/PS1 iNOS (−/−) mice (FIG. 1A, B). In addition, pharmacological treatment of APP/PS1 animals with L-NIL protected from increased reference memory errors and to some extent from working memory error (FIG. 1A, B).

iNOS Deletion has no Effect on Aβ Processing in Preplaque Mice

Figure 1C:
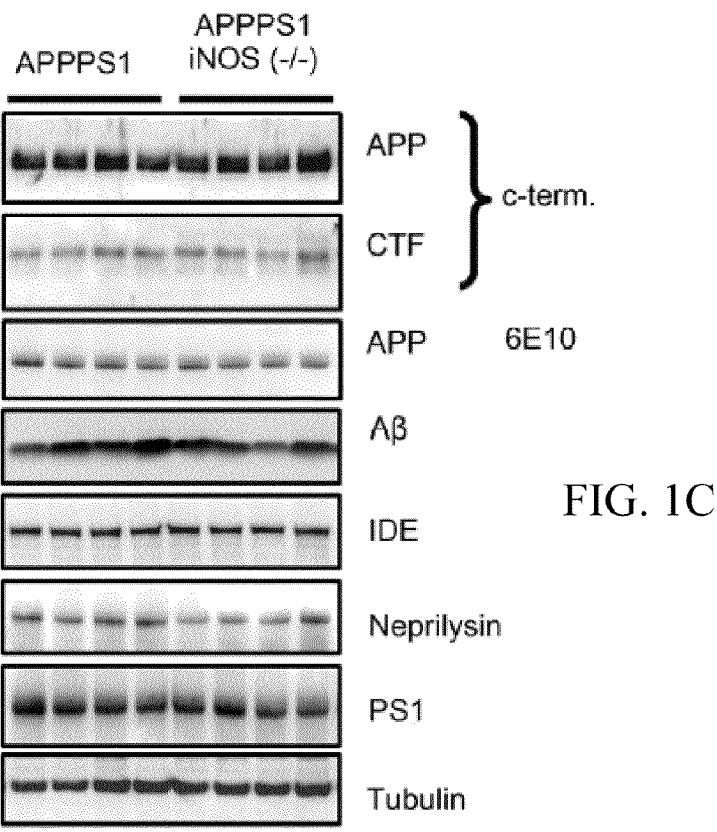
Figure 1D:
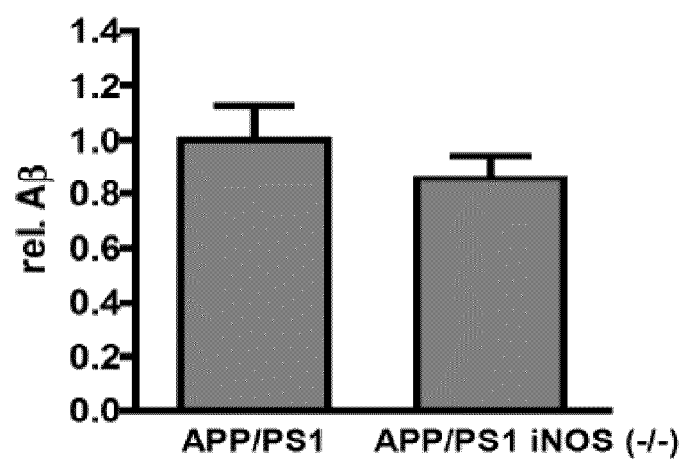
Figure 1E:
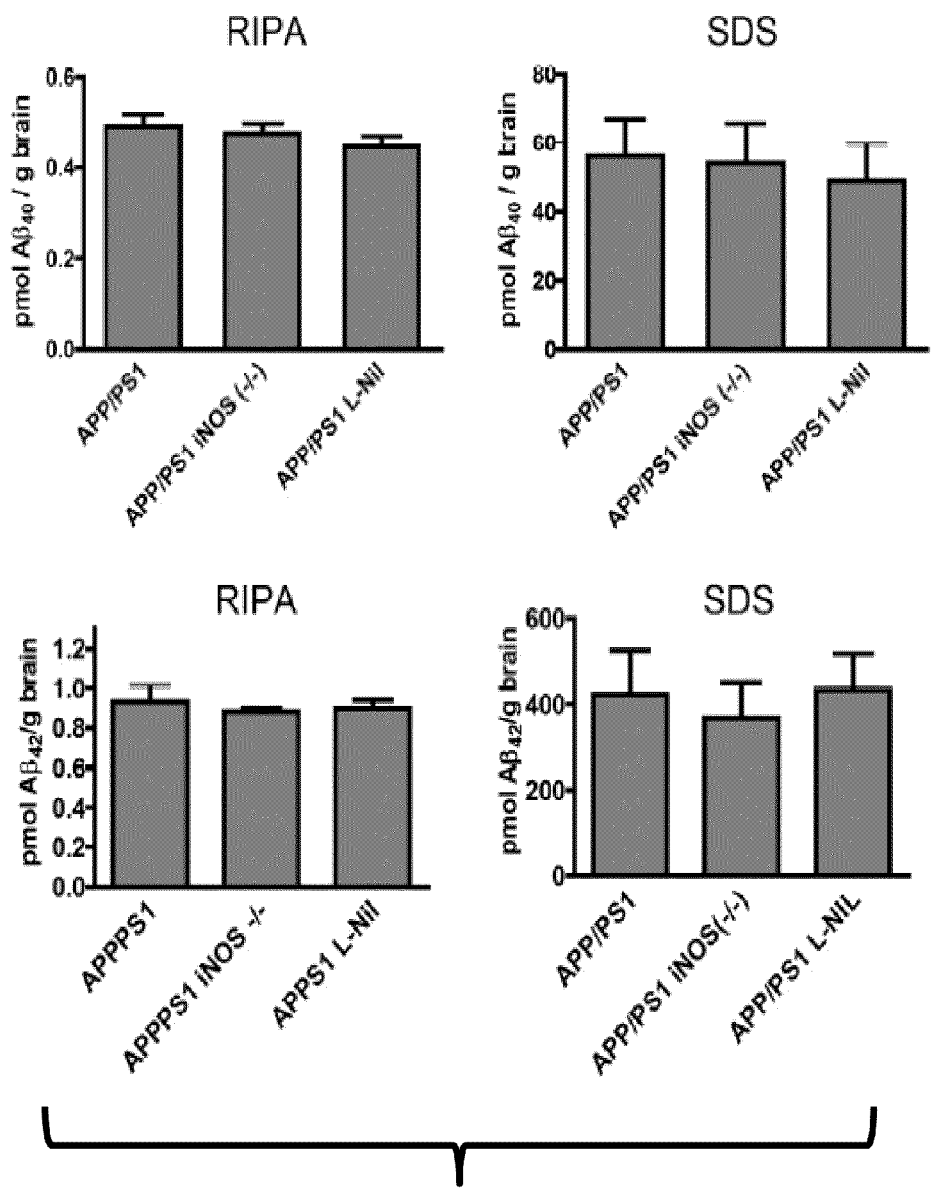
Figure 2A:
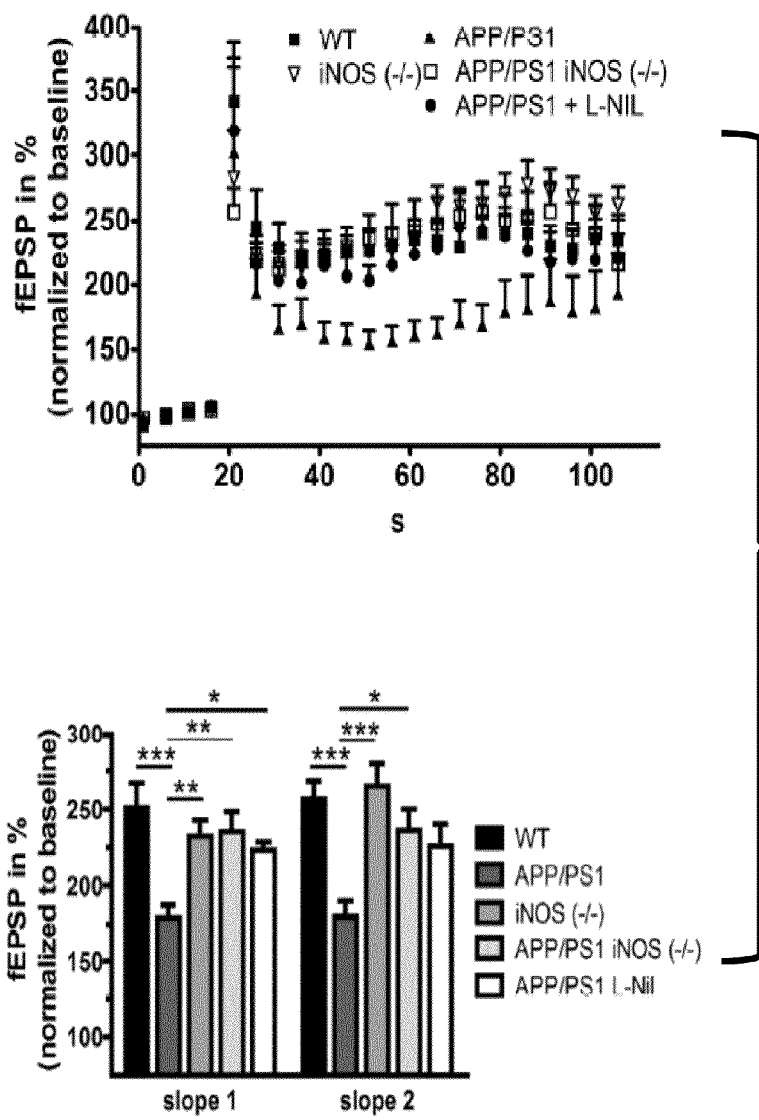
Figure 2B:
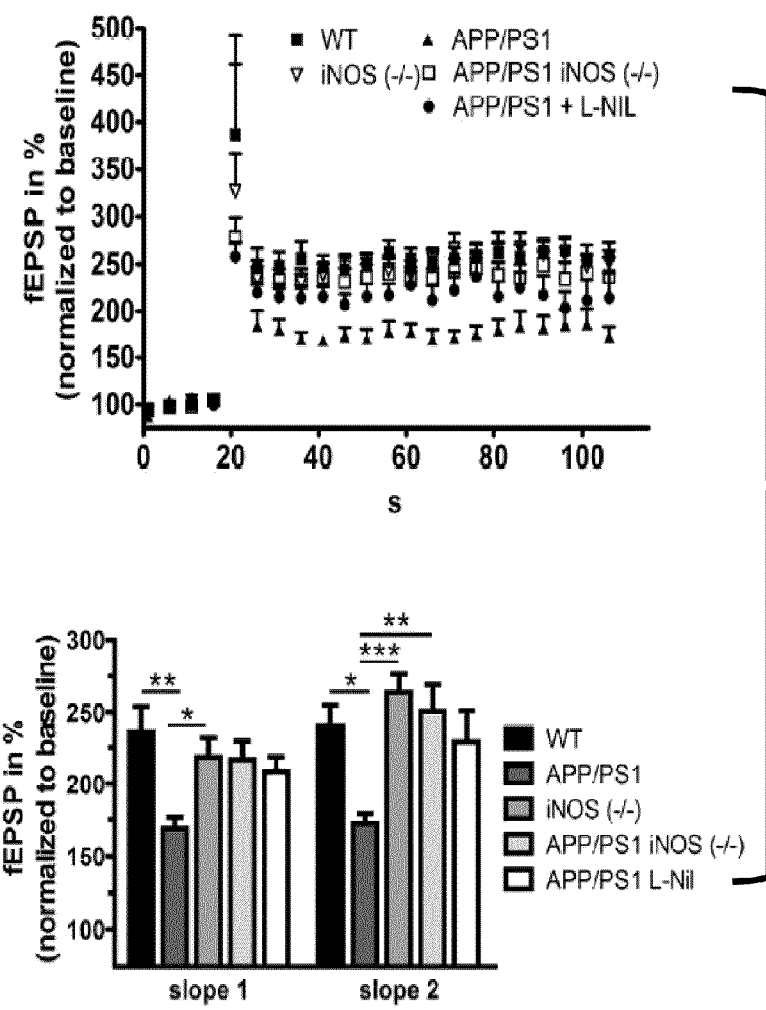
Figure 2C:
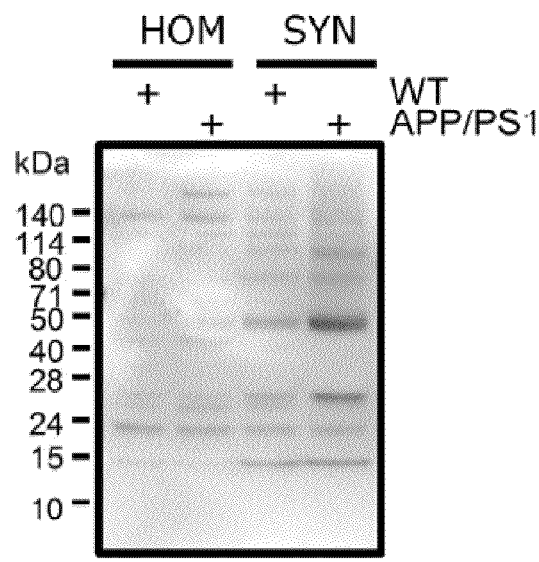
Figure 2D:
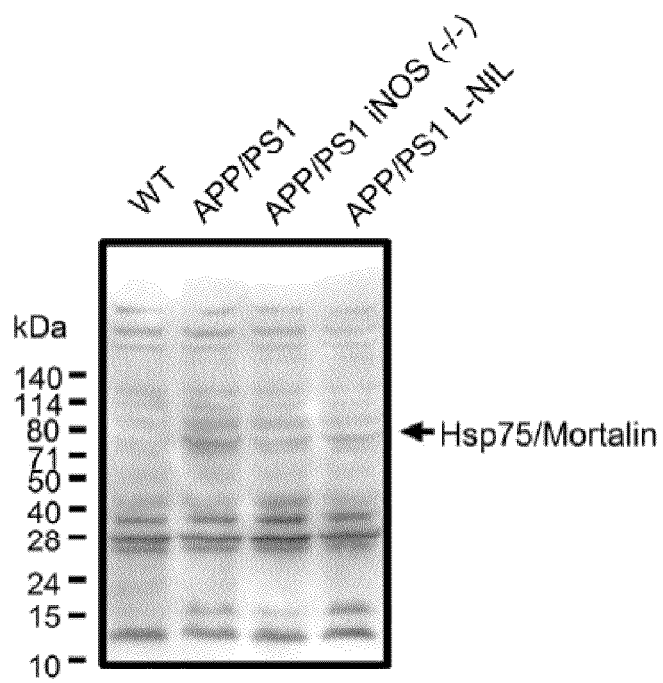
Figure 3A:
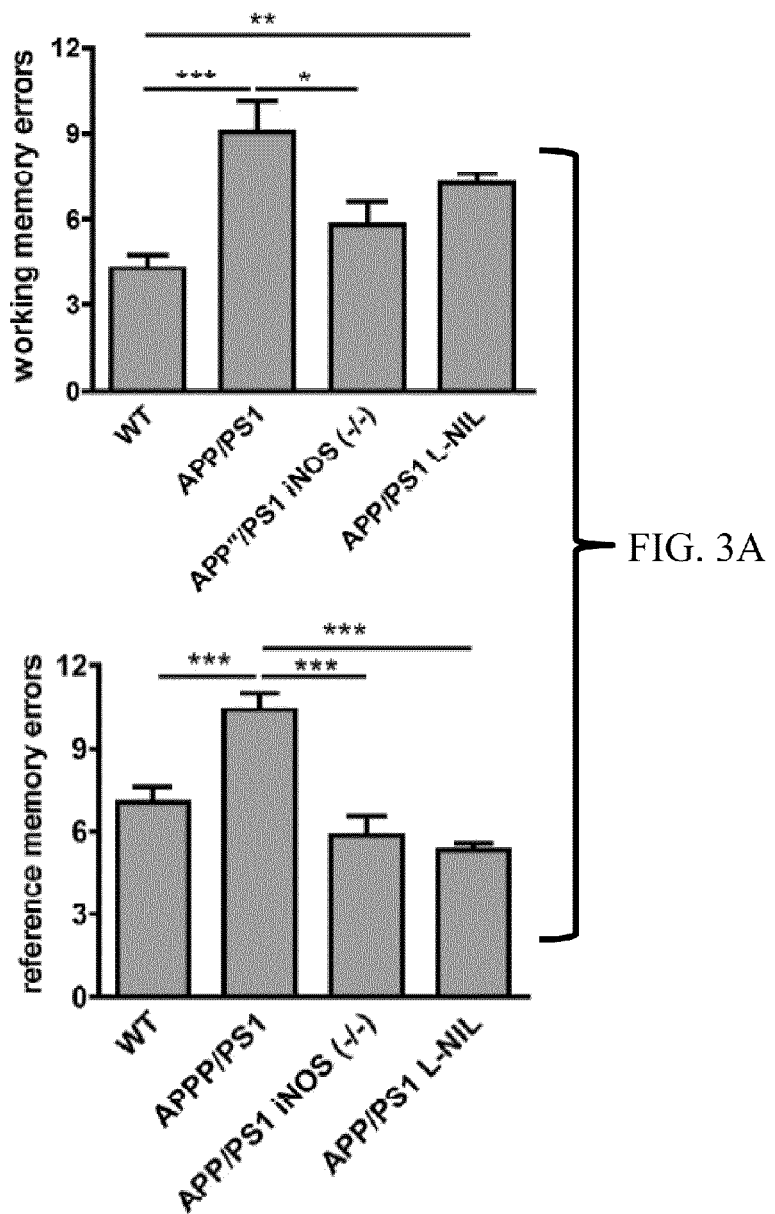
Figure 3B:
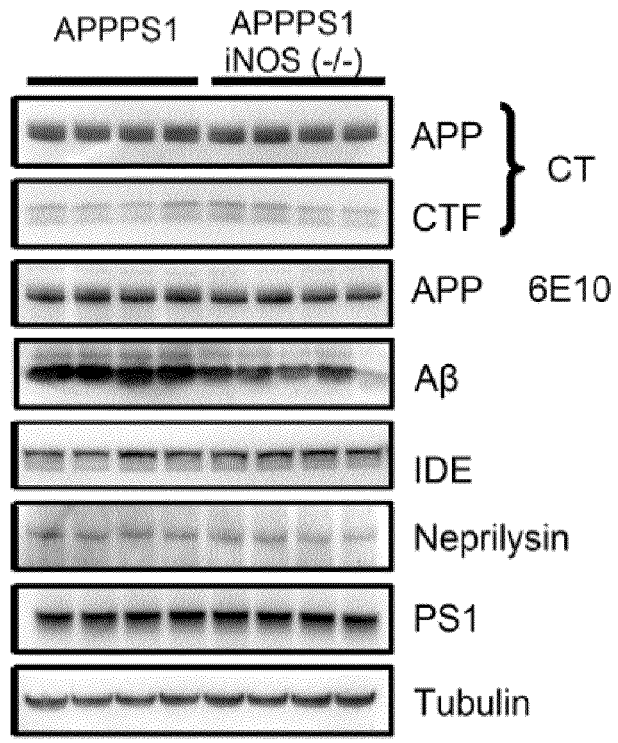
Figure 3C:
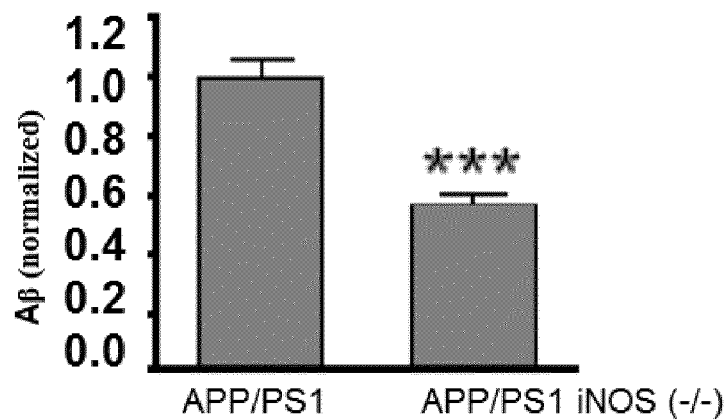
Figure 3D:
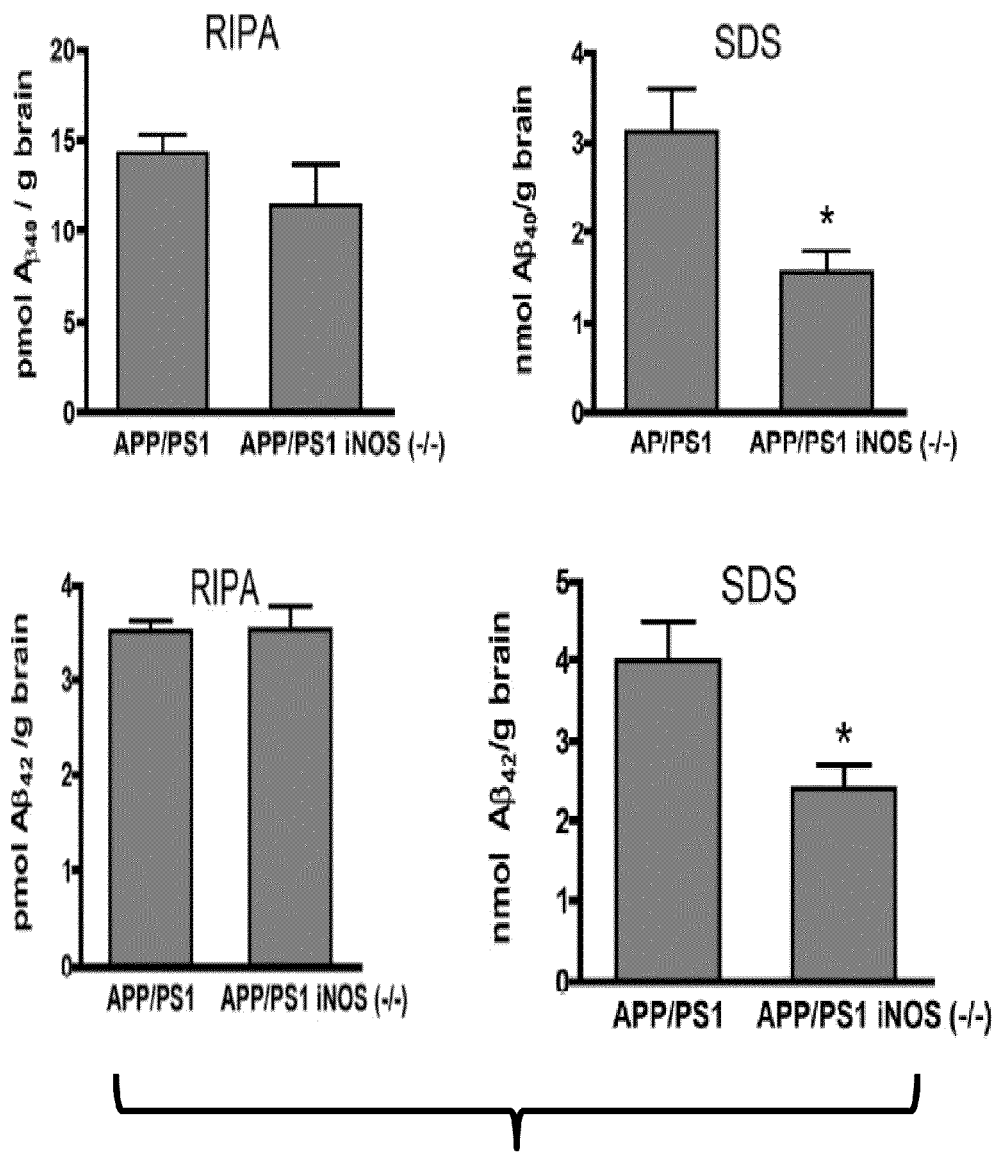
Figure 3E:
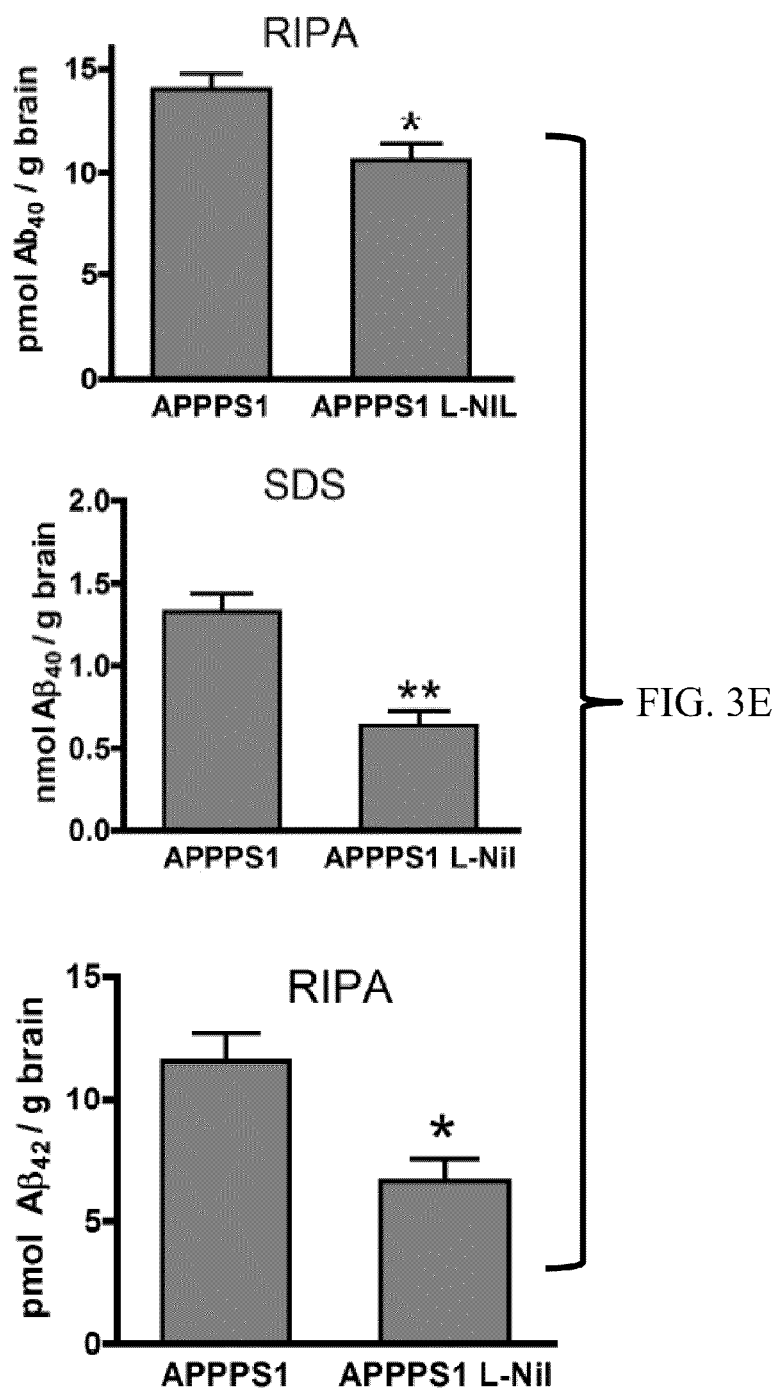
Figure 3F:
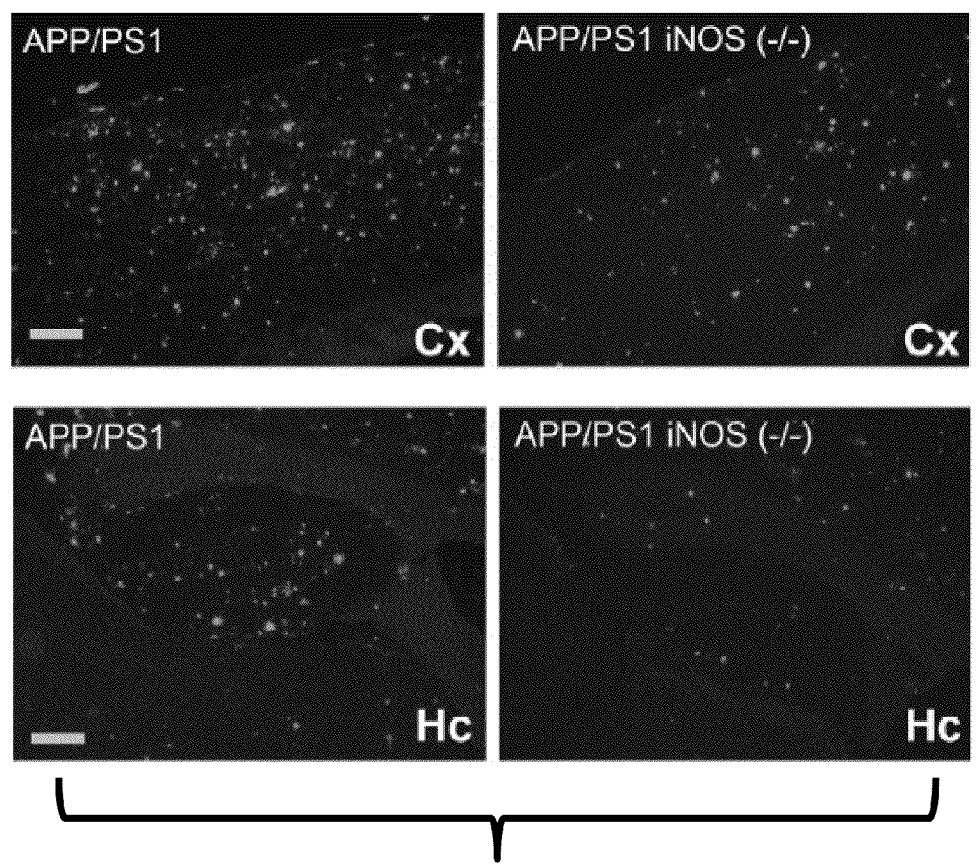
Figure 3G:
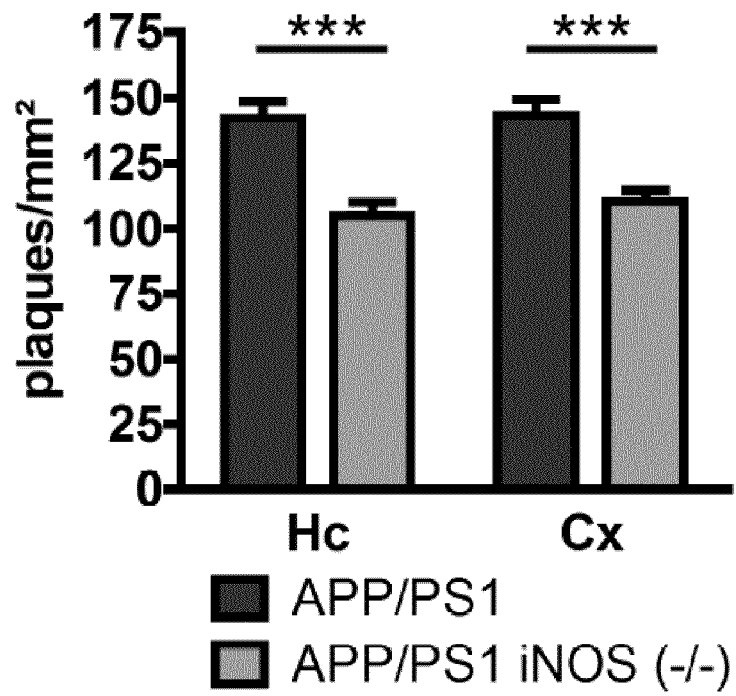
Figure 4A:
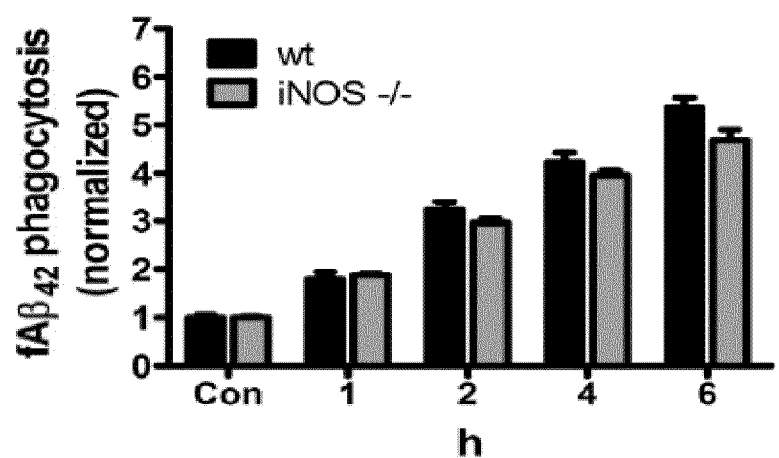
Figure 4B:
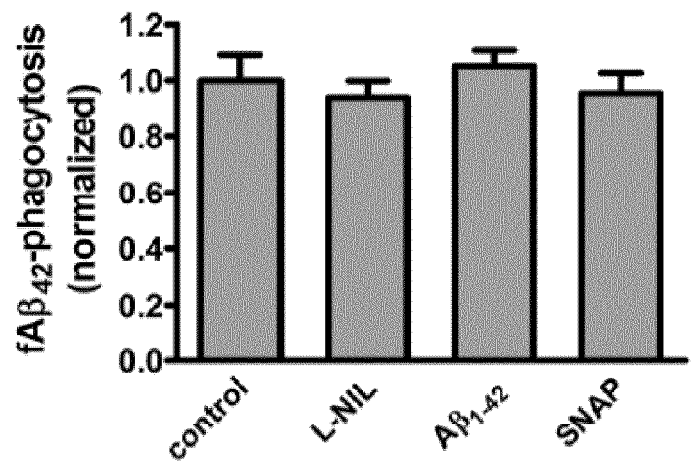
Figure 4C:
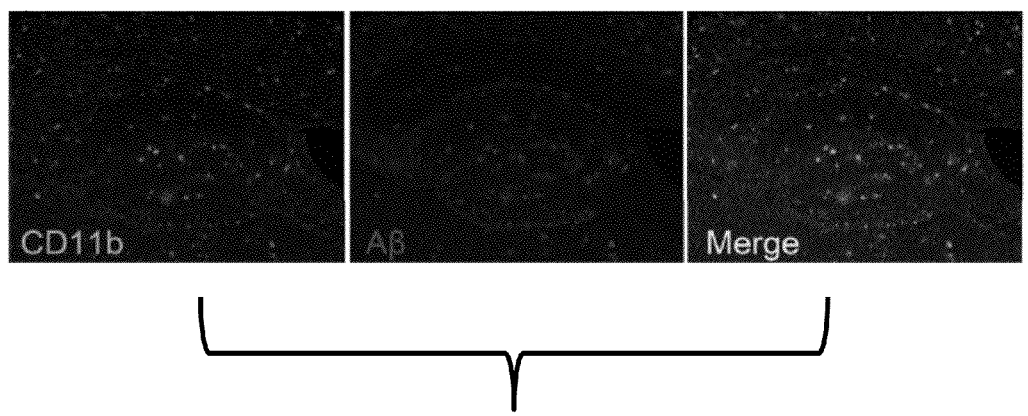
Figure 4D:
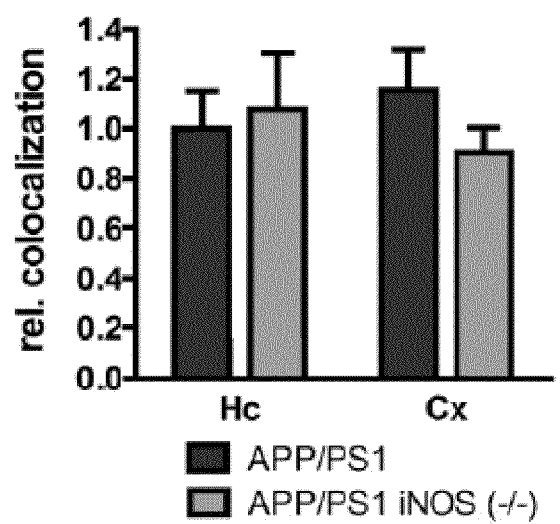
Figure 5A:
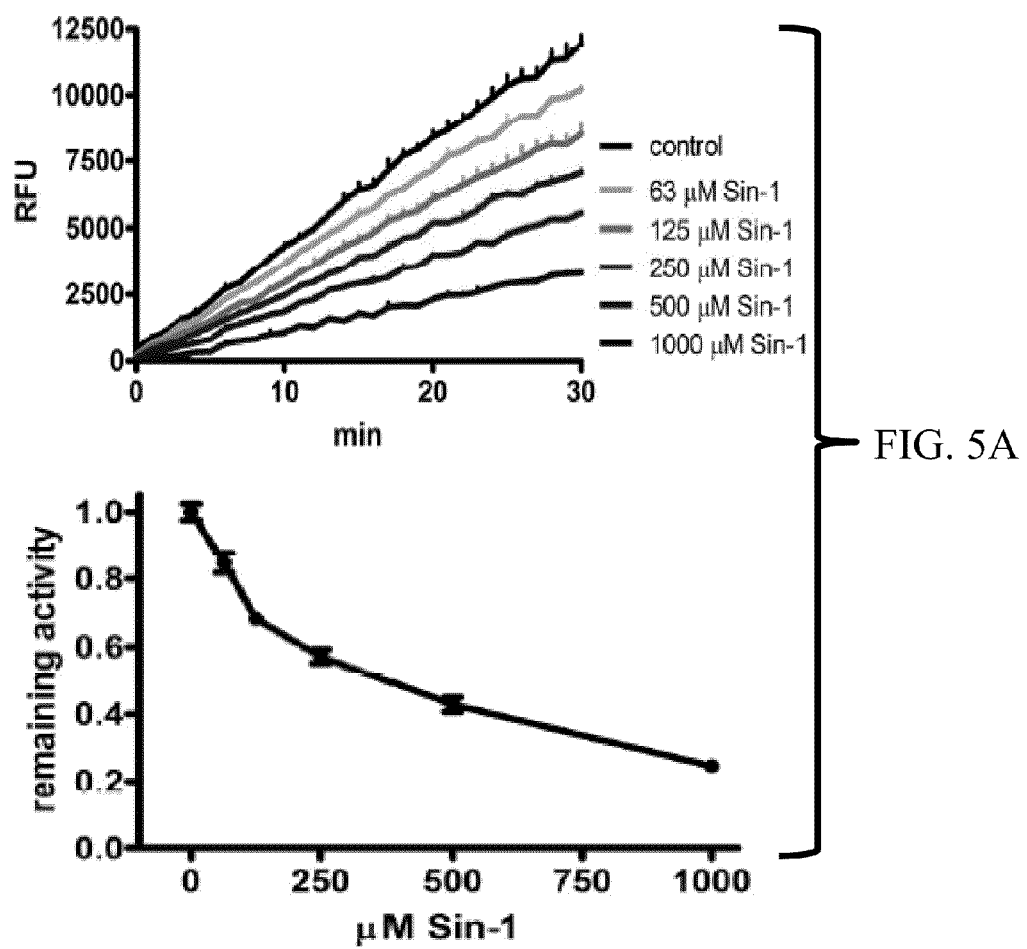
Figures 5B, 5C:
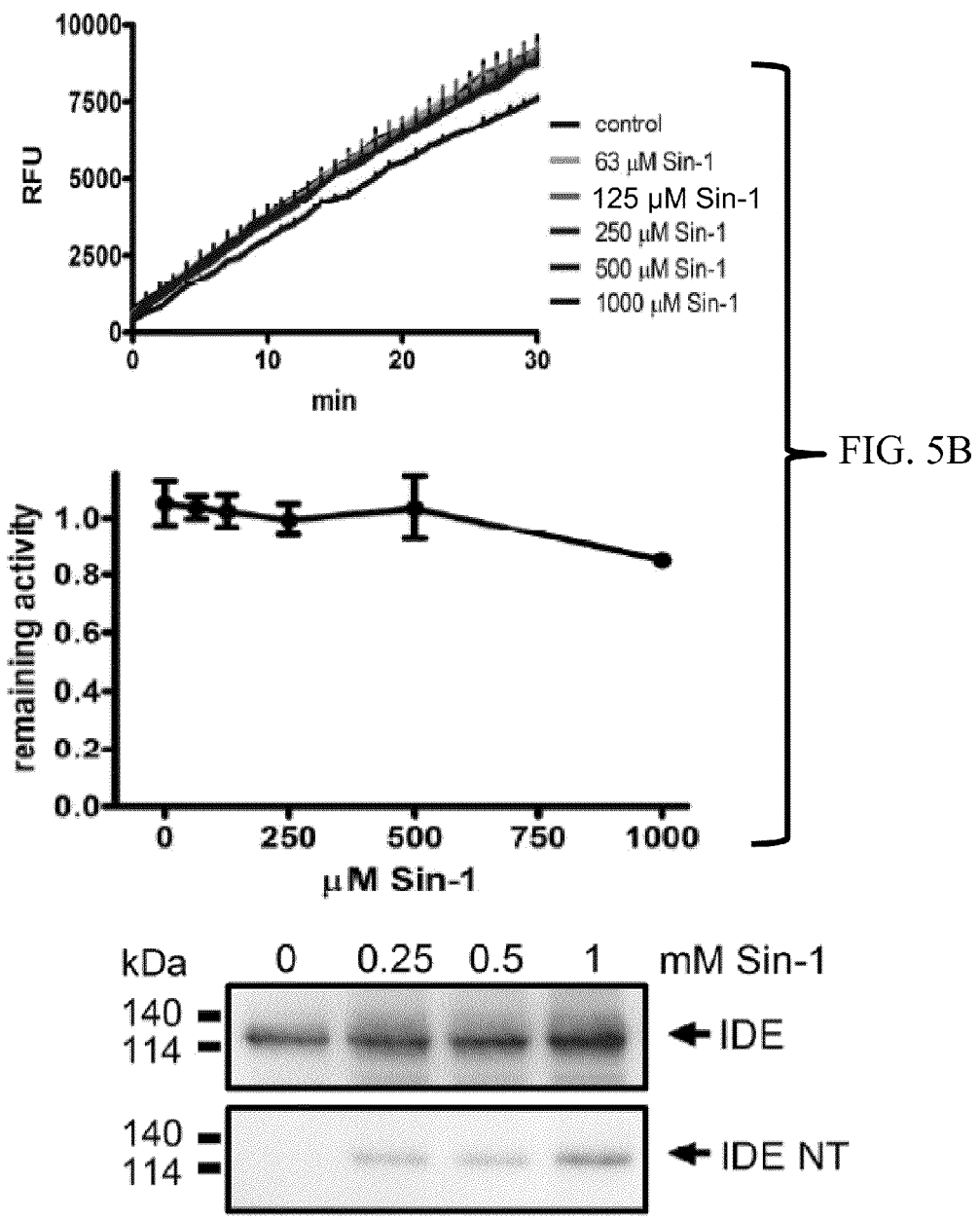
Figure 5D:
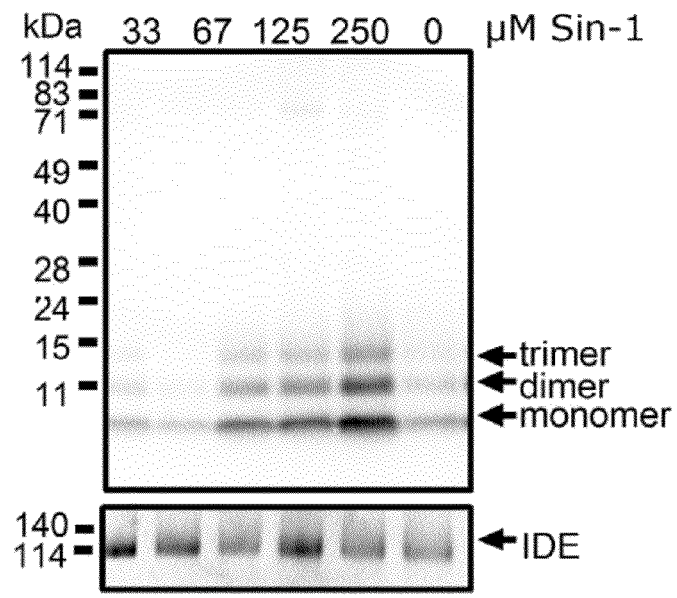
Figure 5E:
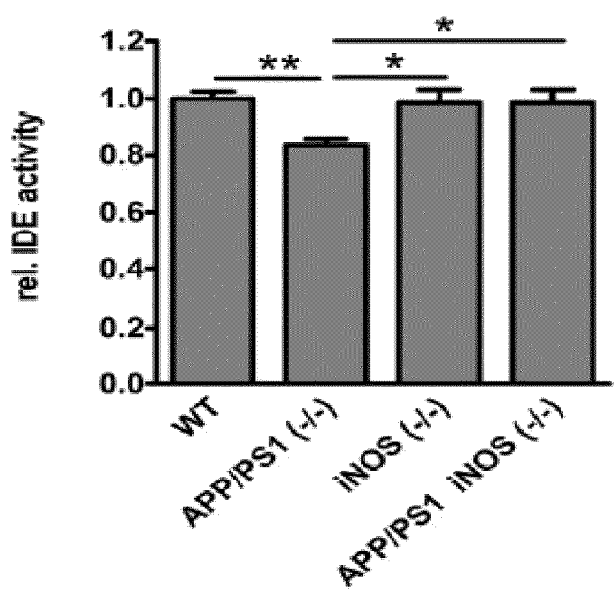
Figure 6A:
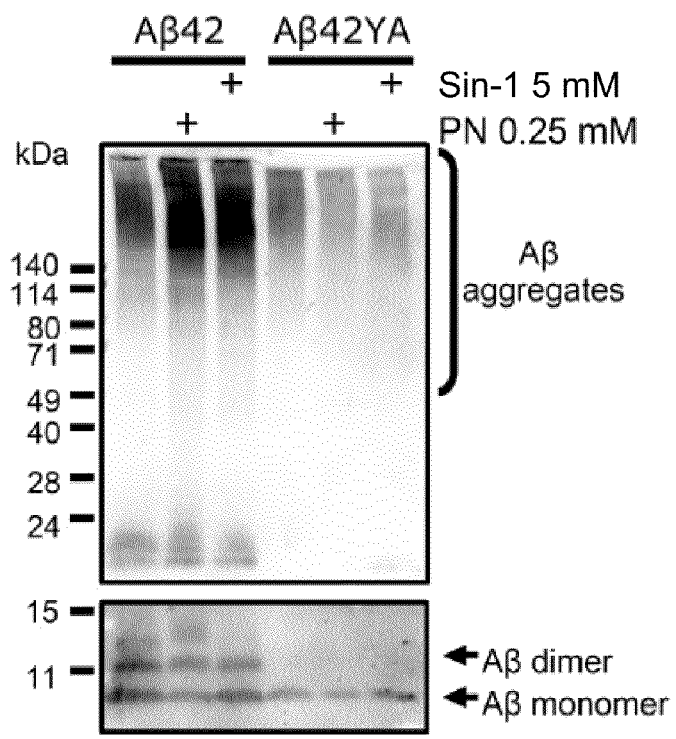
Figure 6B:
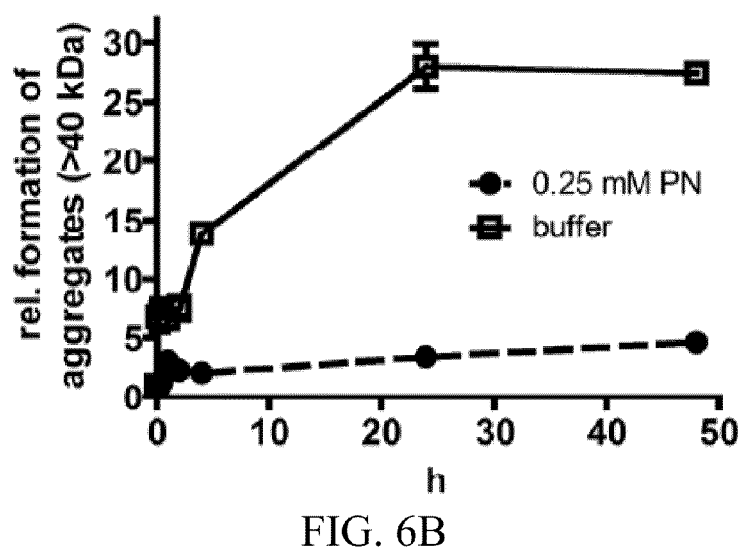
Figure 6C:
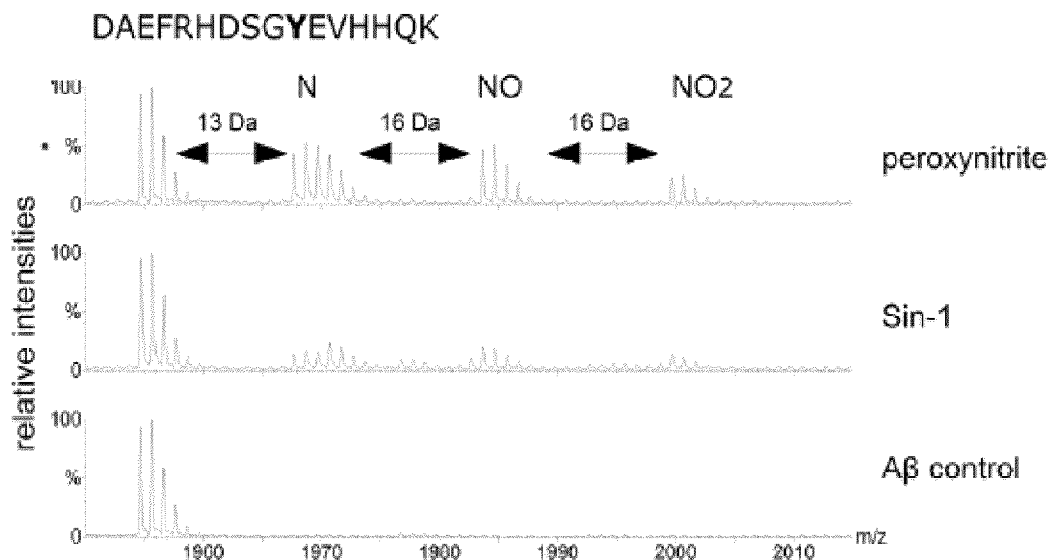
Figure 6D:
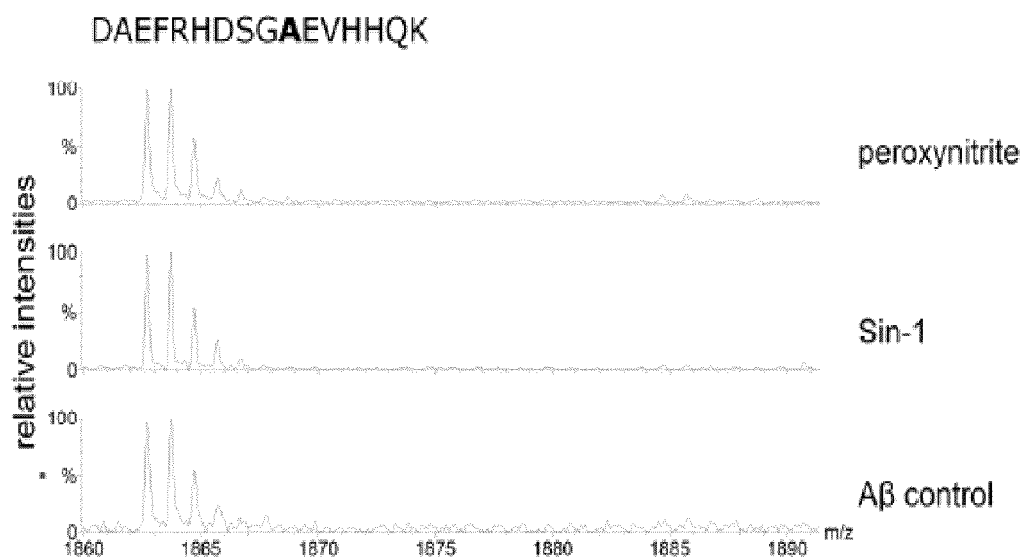

The inventors analyzed APP processing of 5 month old mice to determine whether the observed changes in spatial memory are due to reduced Aβ levels. The inventors observed no changes in APP expression, the formation of APP C-terminal fragments as well as in the expression of two important Aβ degrading enzymes neprilysin and insulin degrading enzyme (IDE) (FIG. 1C, D). Finally, the inventors were unable to detect any changes in the levels of insoluble and soluble Aβ40 and Aβ42 by ELISA in APP/PS1 iNOS (−/−) as well as in APP/PS1 mice preventively treated with L-NIL (FIG. 1E). These data suggest that, even so loss of iNOS protects from the behavioral phenotype caused by the APP/PS1 transgene.

LTP Disturbance in APP/PS1 Mice are Rescued by iNOS Deficiency

Previously, it has been shown that Aβ oligomers inhibit hippocampal LTP therefore resulting in decreased synaptic plasticity[9-11]. As long term potentiation (LTP) is a known mechanism for the formation of spatial memory the inventors determined the early and late response of the CA1 region of the hippocampus in response to an extracellular stimulus of the Schaffer's collaterals in 3 month old mice. The response of hippocampal slices derived from APP/PS1 mice showed a significant reduction in the early and late phase of LTP (10 and 60 minutes after induction, respectively) which was not existent in wild type, iNOS deficient or L-NIL treated mice (FIG. 2 A, B).

Increased Nitrosylation of Synaptosomal Proteins in APP/PS1 Mice

Reduction of LTP is a consequence of changes at the synapse. In is likely that in the APP/PS1 iNOS (−/−) mouse these changes are mediated by the decreased nitrosylation of proteins. Detection of nitrosylated synaptic proteins from synaptosomal fractions of APP/PS1 animals using a s-nitrocystein specific antibody revealed increased s-nitrosylation of these fraction in comparison to age matched wild type mice (FIG. 2 C). In a subsequent approach the inventors immunoprecipitated s-nitroslyated proteins from synaptosomes using the aforementioned anti-body. Immunoprecipitates were separated by SDS-PAGE following analysis of the excised bands by mass spectrometry. The inventors independently purified three times the chaperone Hsp75/mortalin from these fractions (FIG. 2 D, E). Since modification of proteins by s-nitrosylation might result in a loss of function, the inventors tested whether the binding of Hsp75 to one of its described partners, Grp94, is impaired in APP/PS1 mice[24]: Conducting coimmunprecipitations of Hsp75 and Grp94 from synaptosomal fraction the inventors observed that binding of Grp94 was prevented in APP/PS1 mice compared to age matched wild type mice (FIG. 2 D). In addition, binding was restored in APP/PS1 iNOS (−/−) mice. These data suggest that NO mediated synaptic damage may be one explanation for the behavioral and physiological deficits observed in APP/PS1 mice.

Behavioral Phenotyping in Aged Mice

Radial arm maze at 12 month of age showed an even stronger protection of the iNOS knock out group for both working and reference memory errors (FIG. 2 A). In addition, the inventors conducted a therapeutic approach by treating post plaque mice from 6-12 month with L-NIL resulting in a reversion of APP/PS1 phenotype concerning reference memory errors (FIG. 2 A).

Decreased Aβ Burden in Aged APP/PS1 iNOS (−/−)

In contrast to the preplaque animals the inventors observed a strong reduction of insoluble Aβ by immunoblot and ELISA of insoluble Aβ 1-40 and Aβ 1-42 by ELISA in 12 month old APP/PS1 iNOS (−/−) and L-NIL treated animals (FIG. 2 B-E). Again the inventors did not see any changes in the expression in neprilysin and IDE at this age (FIG. 2 B). The inventors could confirm the reduction in the neocortex and hippocampus by measuring the plaque load by thioflavin S staining in APP/PS1 iNOS (−/−) mice (FIG. 2 F, G).

Impact of Nitric Oxide on Aβ Pagocyosis

One possible mechanism for the reduction in Aβ could be the increased phagocytosis by microglia in the brain. The inventors therefore performed in vitro phagocytosis assays using primary microglia from wild type and iNOS (−/−) mice. The inventors could not detect changes in the uptake of aged fibrillar FAM-labeled Aβ1-42 in these cells over a time period of 6 h (FIG. 4 A). Incubation of these cells with either an NO donor (SNAP), an iNOS inhibitor (L-NIL) nor using Aβ itself as an inductor of iNOS resulted in changed phagocytosis of FAM-Aβ1-42 (FIG. 4 B). Finally, the inventors evaluated serial brain sections from APP/PS1 and APP/PS1 iNOS (−/−) mice immunostained for the microglial marker CD11b and Aβ by confocal microscopy. Again, the inventors were not able to detect changes in colocalization, meaning the amount of Aβ inside microglia remained constant (FIG. 4 C, D).

Nitric Oxide Selectively Impairs IDE Activity In vitro and In vivo

Since the discovery of nitric oxide as a signaling ligand there have been speculation about the role of nitric oxide as a modulator of enzyme activity. The inventors therefore asked whether the activity of two Aβ degrading enzymes namely, insulin degrading enzyme (IDE) and neprilysin is affected by nitric oxide. Using an fluorogenic substrate assay the inventors determined the activity of both enzyme after incubation with definite concentration of the NO releaser Sin-1. The inventors observed an inhibitory effect of Sin-1 on IDE activity, which resulted in almost complete inhibition at 1 mM Sin-1 (FIG. 5 A). Of note, the steady state concentration of peroxynitrite is only up to 3.6% of the added Sin-1 concentration[25]. Surprisingly, the inventors could not detect any impact of NO on the activity of neprilysin (FIG. 5 B). Iincubation of Sin-1 with purified recombinant IDE resulted in modifications of IDE detectable with an nitrotyrosine specific antibody by immunoblotting (FIG. 5 C). To determine the effect of Sin-1 on the degradation of Aβ, the inventors preincubated IDE with Sin-1 for 30 min. followed by addition of Aβ1-42. Analysis after 2 h of incubation showed decreased degradation of Aβ with increasing concentration of Sin-1 (FIG. 5 D).

To verify this finding in vivo the inventors measured the activity of IDE in lysates of 12 month old wild type, APP/PS1, iNOS (−/−) and APP/PS1 iNOS (−/−) animals using a IDE specific fluorogenic substrate[21]. To eliminate any residual activity of neprilysin, the inventors performed the assay in the presence of the asparyl protease inhibitor phosphoramidon. In accordance with our in vitro finding the inventors observed a decrease in IDE activity by the APP/PS1-transgene that was rescued by the deletion of iNOS (FIG. 5 E).

Nitration of Aβ Accelerates its Aggregation

It is known that the overepression of murine APP in mice does not result in amyloid deposition. In addition, it has been shown that N-terminal modification of Aβ increase the ability of Aβ to form high molecular weight aggregates[26,27]. There are three amino acids within the amyloid domain of APP that differ from the murine protein. One of these amino acids is the tyrosine 10 that is missing in mouse APP. The inventors therefore hypothesized, that nitration of this amino acid under conditions of activated iNOS results in accelerates the formation of Aβ. Incubation of synthetic Aβ with the either peroxynitrit or with the NO releaser Sin-1 resulted in strong induction of high molecular weight aggregated that were missing after incubation using the Aβ with an tyrosine to alanine mutation (AβY10A) (FIG. 6 A). Quantification over time revealed an x-fold increase within 24 h after peroxynitrite treatment (FIG. 6 B). Mass spectrometry analysis of nitrated Aβ revealed the typical pattern for nitrated peptide, that was missing in the AβY10A peptide (FIG. 6 C).

Detection of 3NT-Aβ in Brains

Figure 7A:
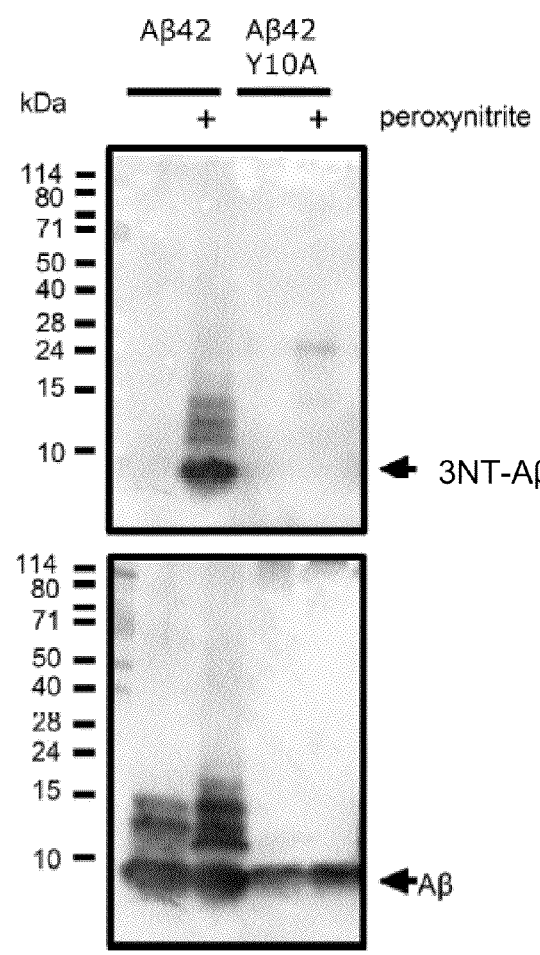
Figure 7B:
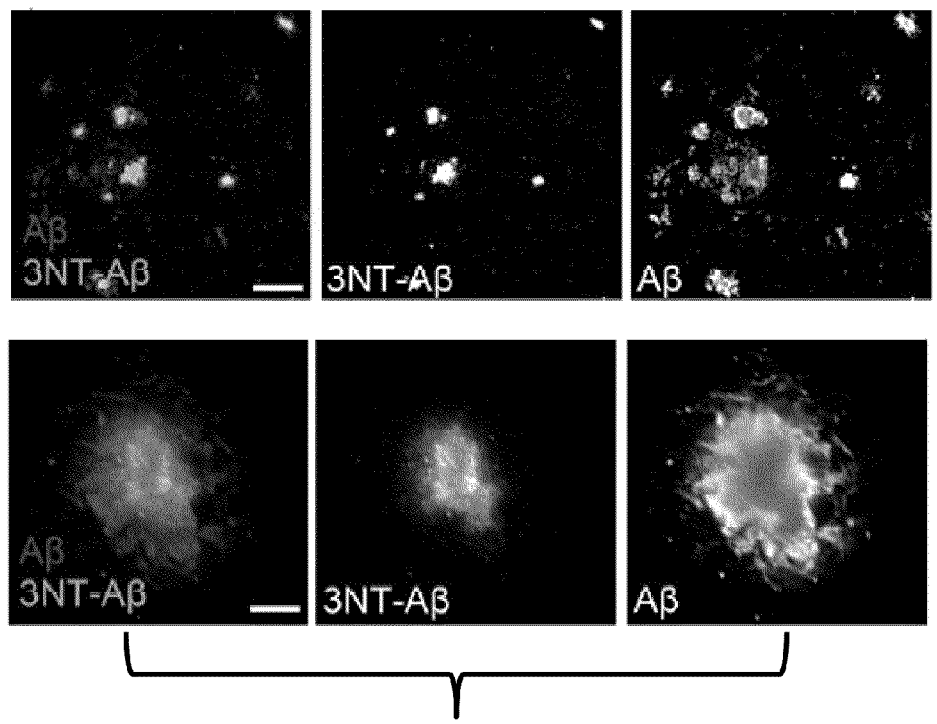
Figure 7C:
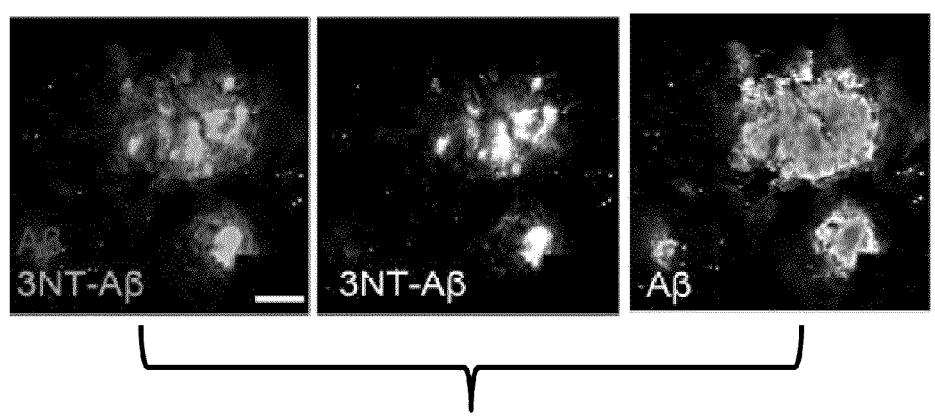
Figure 7D:
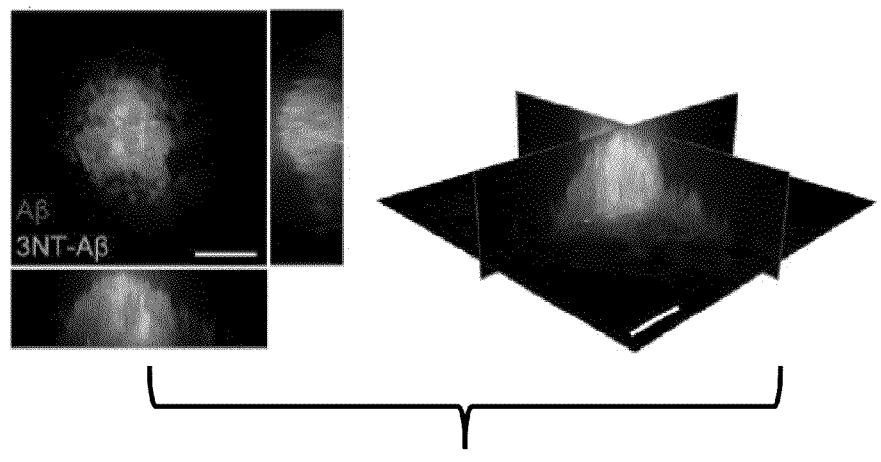
Figure 7E:
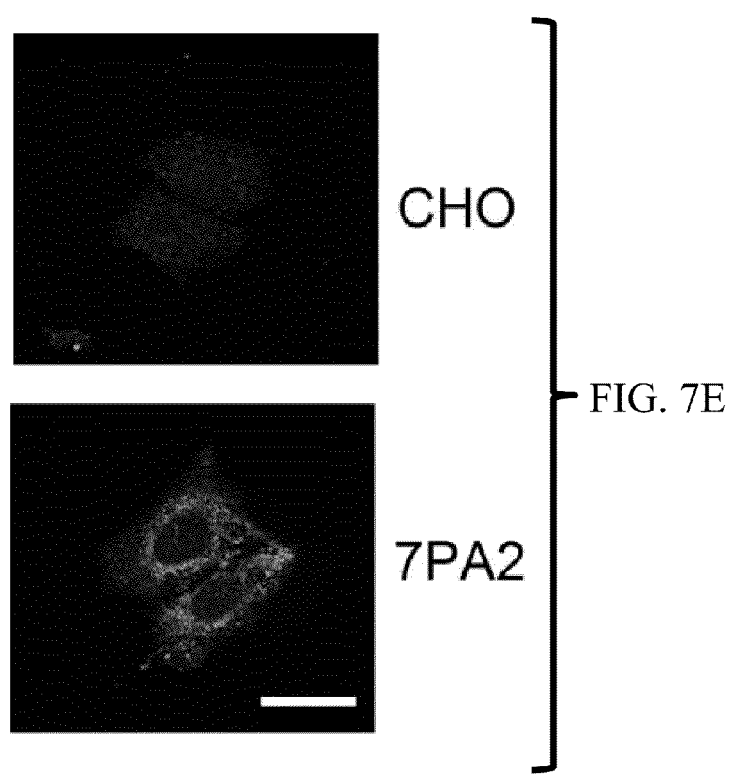
Figure 7F:
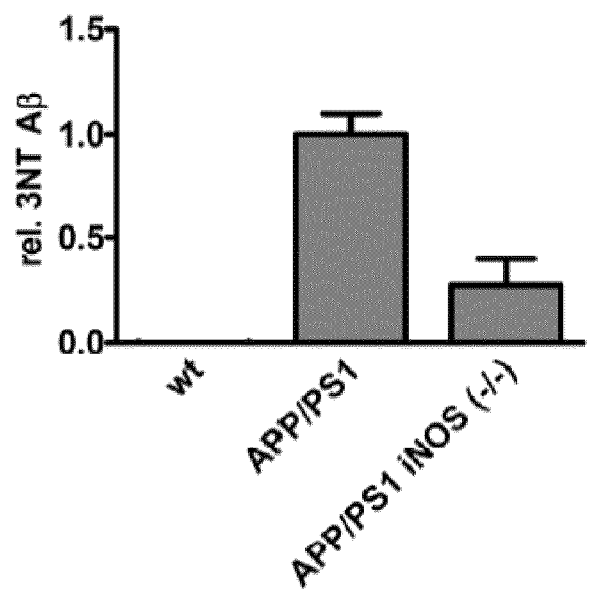

To detect nitrated Aβ in mice, the inventors generated an antibody specifically recognizing Aβ nitrated at the tyrosine at position 10 (anti-3NT-Aβ). This double immuno-purified serum, first against the nitrated peptide and subsequently against the non-nitrated peptide specifically recognizes nitrated Aβ, whereas there is no immunoreactivity towards non-nitrated or Aβ containing a tyrosine to alanine mutation at position 10 by western blotting (FIG. 7 A). The inventors then used this 3NT-Aβ antibody on brain sections of APP/PS1-transgenic mice at plaque age (12 month) (FIG. 7 B) and 18 month (FIG. 7C). The inventors observed strong staining of plaques as verified by costaining with antibody IC16 against Aβ. The immunoreactivity was exclusively localized to the core of the plaque (FIG. 7 D). Since the inventors could not detect 3NT-Aβ within cells, the inventors used cell line 7PA2 which is known produce natural oligomers of human Aβ within specific intracellular vesicles[28]. Staining if these cells using the 3NT-Aβ antibody revealed a strong immunreactivity within the cells that was absent in untransfected CHO cells suggesting that the nitration and thereby aggregation of Aβ starts in an intracellular compartment (FIG. 7 E). In addition, the inventors measured the amount of 3NTAβ in SDS fractions of wild type, APP/PS1 and APP/PS-1 iNOS(−/−) animals by sandwich ELSIA. There was no measurable amounts if this peptide in wild type animals, but in the APP/PS1 animals. In turn, mice lacking iNOS (−/−) showed a 74% reduction of 3NT-Aβ reactivity (FIG. 7 F), which was higher than the total reduction of Aβ that the inventors observed before (FIG. 3 B-E).

Figure 8A:
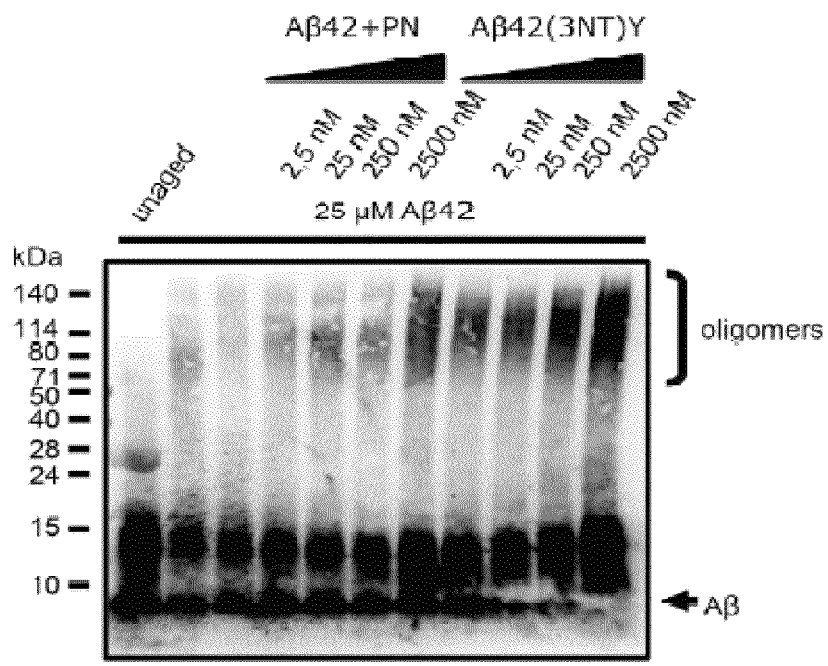
Figure 8B:
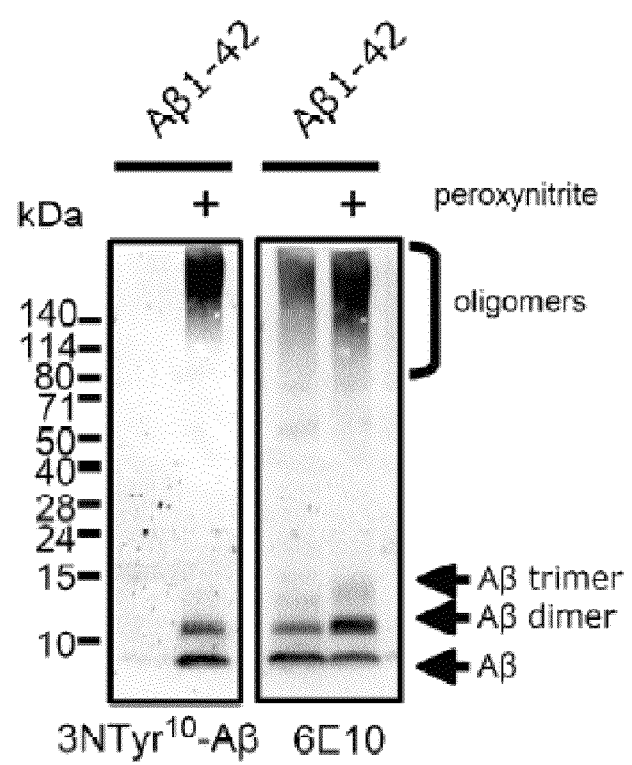
Figure 8C:
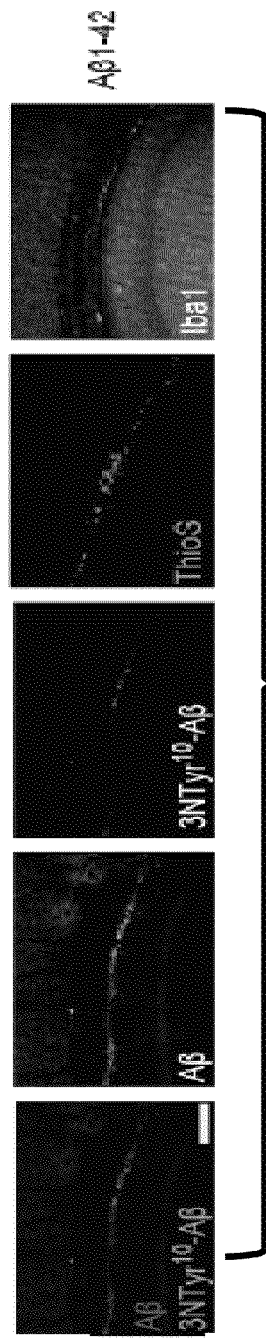
Figure 8D:
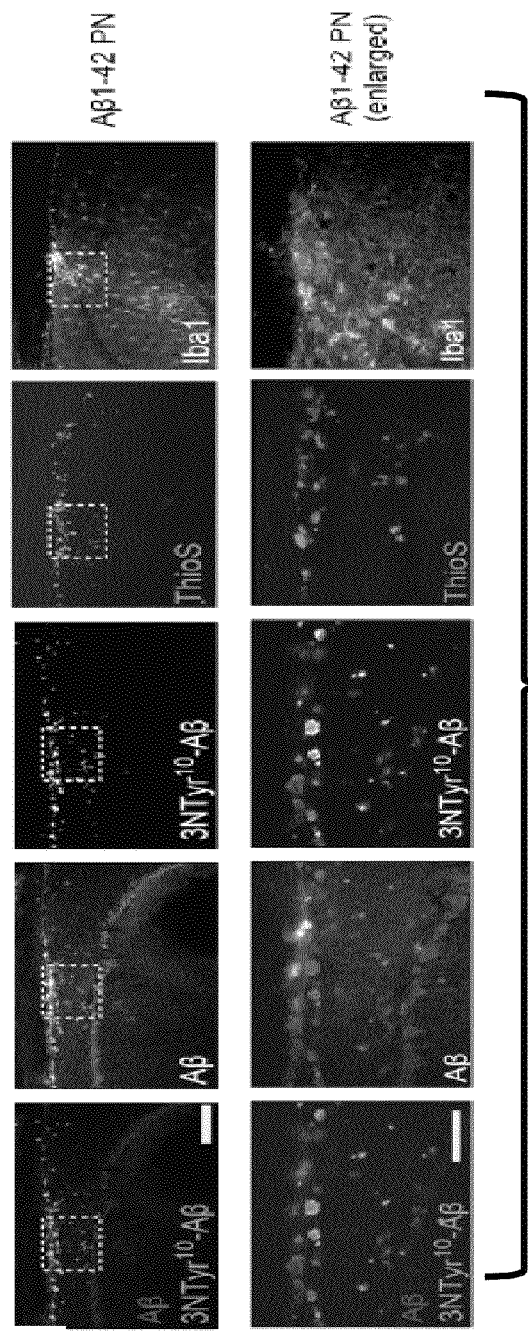
Figure 8E:
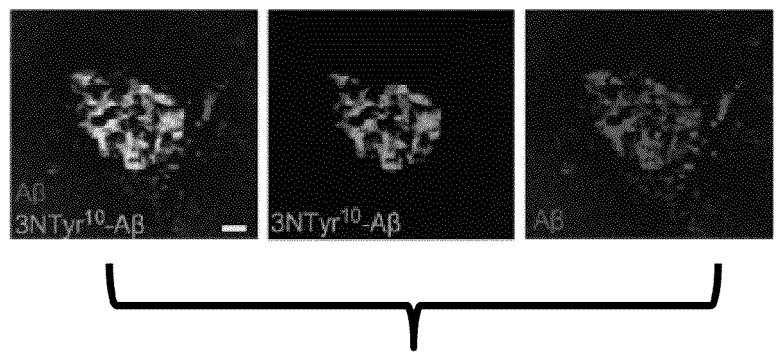

In vitro Aβ1-42 aggregation assays revealed that addition of small amounts of nitrated Aβ1-42 species resulted in the increased formation of Aβ oligomers (FIG. 8A). To test the hypothesis in vivo that nitrated Aβ acts as an amyloid seed in APP/PS1-transgenic animals, the inventors injected 2.5 μl of a 0.5 mg/ml solution of either Aβ1-42 or nitrated 6 Aβ1-42 into the brain of 2.5 month old APP/PS1 mice. Verification of the injected Aβ peptides by Western blot demonstrated their nitration status using the 3NTyr10-Aβ antibody and increased formation of Aβ oligomers using antibody 6E10 (FIG. 8B). Analysis after 8 weeks showed strong 3NTyr10-Aβ immunoreactivity in case of the mice injected with nitrated Aβ1-42 (FIG. 8D). In addition, nitrated Aβ1-42 was able to induce amyloid seeds that were localized distant from the injection side (FIG. 8D), that were missing in mice injected with non-nitrated Aβ (FIG. 8C). These seeds were composed of nitrated Aβ surrounded by non-nitrated Aβ (FIG. 8E), thus mimicking the immunomorphological appearance of plaques detected in AD brains. This species also evoked a increase of Iba1 suggesting a role for microglial activation.

Immunohistochemical Analysis of Human AD and Control Brains

To detect Aβ nitrated at tyrosine 10 (3NTyr10-Aβ), we generated an antiserum specifically recognizing this epitope (3NTyr10-Aβ antiserum). This antiserum showed strong immunoreactivity against peroxynitrite treated Aβ1-42 peptide or synthetically-nitrated Aβ1-42 (Aβ42(3NT)Y), which was absent in case of the untreated peptide (FIG. 9A). We observed a low amount of reactivity when treating Aβ1-42Y10F mutant peptide with peroxynitrite. This might be caused by the conversion of phenylalanine to tyrosine by hydroxyl radicals generated during the decomposition of peroxynitrite. In accordance with this, there was no reactivity towards Aβ1-42 bearing a Y10A mutation after incubation with peroxynitrite.

Immunohistochemical analysis of AD and control brains by 3NTyr10-Aβ antiserum revealed a lack of immunoreactivity in control brains, whereas in AD brain the core of amyloid plaques was intensively labeled, as confirmed by IC16 double staining (FIG. 9B). Measuring the relative amounts of 3NTyr10-Aβ by sandwich ELISA in insoluble fractions of human brain samples, the inventors detected 3NTyr10-Aβ in the SDS-fraction of AD patients, and only to very low amount in non-demented controls (FIG. 9C). Further, the relative signal ratio of 3NTyr10-Aβ between control and AD patients was comparable to that of Aβ1-42 (FIG. 9C)

Nitration of Aβ at Tyrosine 10 Induces its Aggregation

Figure 10A:
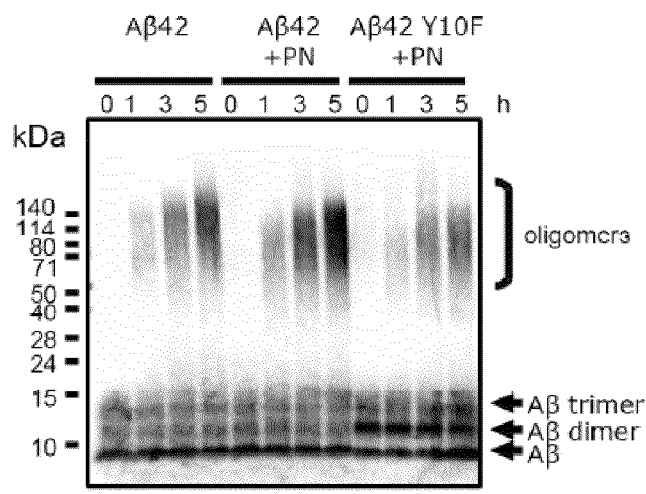
Figure 10B:
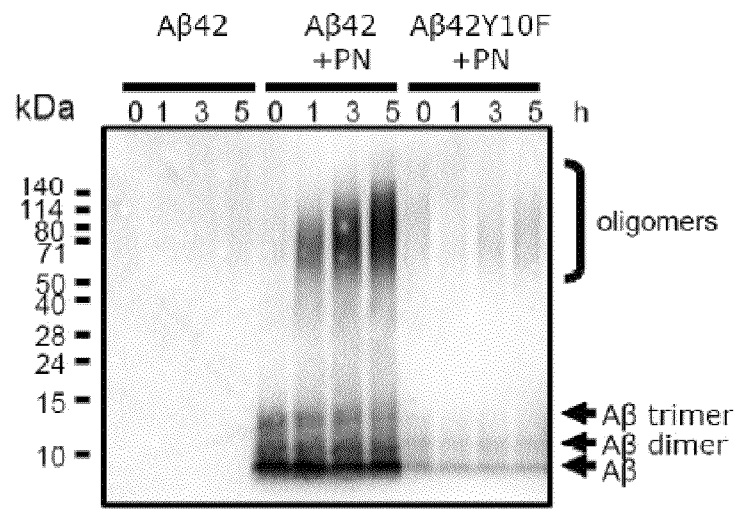
Figure 10C:
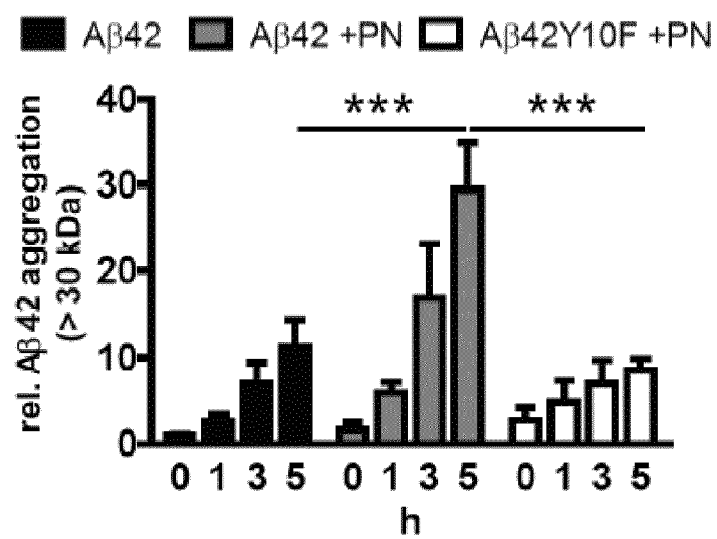
Figure 10D:
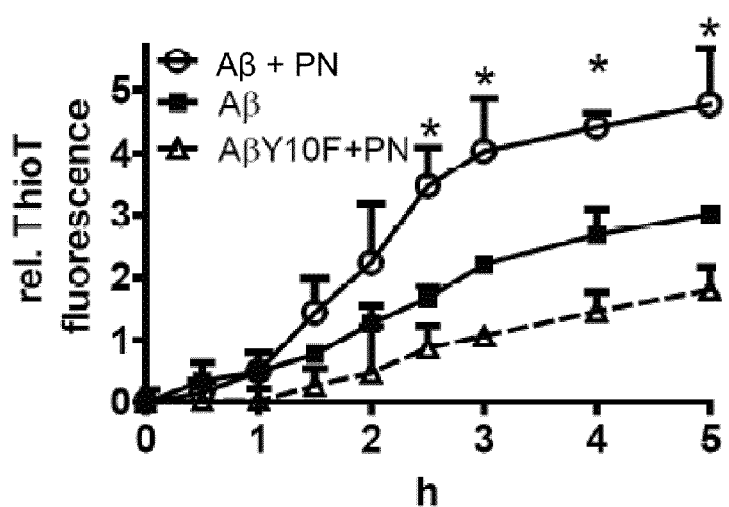

Since N-terminal modifications of Aβ have been shown to induce its aggregation, the inventors speculated whether nitration of Aβ has a similar effect. Indeed, incubation of synthetic Aβ1-42 with peroxynitrite or the NO donor Sin-1 resulted in increased generation of high molecular weight SDS-resistant oligomers (FIG. 10A). Using Aβ1-42 peptides with a tyrosine to alanine or phenylalanine mutation (Aβ42Y10A or Aβ42Y10F) reduced aggregation to the level of untreated Aβ1-42 (FIG. 10A). In case of the non-mutated Aβ1-42 the inventors observed the incorporation of nitrated Aβ1-42 into oligomers (FIG. 10C). There was a very low amount of nitrated Aβ1-42Y10F detectable using the 3NTyr10-Aβ antiserum. Finally, the inventors confirmed the Western blot results by detecting an increased formation rate of β-sheet amyloid fibril structures of nitrated Aβ1-42 using thioflavin T (FIG. 9B), which was prevented using the Aβ42Y10F peptide treated with peroxynitrite.

LITERATURE REFERENCES AS CITED

1. Stamler, J. S. et al. (S)NO signals: translocation, regulation, and a consensus motif. *Neuron* 18, 691-696 (1997).
2. Vodovotz, Y. et al. Inducible nitric oxide synthase in tangle-bearing neurons of patients with Alzheimer's disease. *J. Exp. Med.* 184, 1425-1433 (1996).
3. Heneka, M. T. et al. Neuronal and glial coexpression of argininosuccinate synthetase and inducible nitric oxide synthase in Alzheimer disease. *J. Neuropathol. Exp. Neurol* 60, 906-916 (2001).
4. Beal, M. F. Energetics in the pathogenesis of neurodegenerative diseases. *Trends Neurosci* 23, 298-304 (2000).
5. Kröncke, K. D., Suschek, C. V. & Kolb-Bachofen, V. Implications of inducible nitric oxide synthase expression and enzyme activity. *Antioxid. Redox Signal* 2, 585-605 (2000).
6. Cho, D. et al. S-nitrosylation of Drp1 mediates beta-amyloid-related mitochondrial fission and neuronal injury. *Science* 324, 102-105 (2009).
7. Hara, M. R. et al. S-nitrosylated GAPDH initiates apoptotic cell death by nuclear translocation following Siahl binding. *Nat. Cell Biol* 7, 665-674 (2005).
8. Uehara, T. et al. S-nitrosylated protein-disulphide isomerase links protein misfolding to neurodegeneration. *Nature* 441, 513-517 (2006).
9. Yao, D. et al. Nitrosative stress linked to sporadic Parkinson's disease: S-nitrosylation of parkin regulates its E3 ubiquitin ligase activity. *Proc. Natl. Acad. Sci. U.S.A* 101, 10810-10814 (2004).
10. Brüne, B., Zhou, J. & von Knethen, A. Nitric oxide, oxidative stress, and apoptosis. *Kidney Int. Suppl* S22-24 (2003).
11. Butterfield, D. A. et al. Elevated levels of 3-nitrotyrosine in brain from subjects with amnestic mild cognitive impairment: implications for the role of nitration in the progression of Alzheimer's disease. *Brain Res* 1148, 243-248 (2007).
12. Castegna, A. et al. Proteomic identification of nitrated proteins in Alzheimer's disease brain. *J. Neurochem.* 85, 1394-1401 (2003).
13. Fernandez-Vizarra, P. et al. Expression of nitric oxide system in clinically evaluated cases of Alzheimer's disease. *Neurobiol. Dis* 15, 287-305 (2004).
14. Tohgi, H. et al. Alterations of 3-nitrotyrosine concentration in the cerebrospinal fluid during aging and in patients with Alzheimer's disease. *Neurosci. Lett* 269, 52-54 (1999).
15. Lüth, H., Münch, G. & Arendt, T. Aberrant expression of NOS isoforms in Alzheimer's disease is structurally related to nitrotyrosine formation. *Brain Res* 953, 135-143 (2002).
16. Nakamura, T. & Lipton, S. A. Cell death: protein misfolding and neurodegenerative diseases. *Apoptosis* 14, 455-468 (2009).

17. Souza, J. M., Peluffo, G. & Radi, R. Protein tyrosine nitration—functional alteration or just a biomarker? *Free Radic. Biol. Med.* 45, 357-366 (2008).
18. Jankowsky, J. L. et al. Co-expression of multiple transgenes in mouse CNS: a comparison of strategies. *Biomol. Eng* 17, 157-165 (2001).
19. Laubach, V. E. et al. Mice lacking inducible nitric oxide synthase are not resistant to lipopolysaccharide-induced death. *Proc. Natl. Acad. Sci. U.S.A* 92, 10688-10692 (1995).
20. Olton, D. S. The radial arm maze as a tool in behavioral pharmacology. *Physiol. Behav* 40, 793-797 (1987).
21. Song, E. et al. Substrate activation of insulin-degrading enzyme (insulysin). A potential target for drug development. *J. Biol. Chem.* 278, 49789-49794 (2003).
22. Chapman, P. F. et al. Impaired synaptic plasticity and learning in aged amyloid precursor protein transgenic mice. *Nat. Neurosci* 2, 271-276 (1999).
23. Moran, P. M. et al. Age-related learning deficits in transgenic mice expressing the 751-amino acid isoform of human beta-amyloid precursor protein. *Proc. Natl. Acad. Sci. U.S.A* 92, 5341-5345 (1995).
24. Takano, S. et al. Identification and characterization of molecular interactions between glucose-regulated proteins (GRPs) mortalin/GRP75/peptide-binding protein 74 (PBP74) and GRP94. *Biochem. J* 357, 393-398 (2001).
25. Martin-Romero, F. J. et al. Fluorescence measurements of steady state peroxynitrite production upon SIN-1 decomposition: NADH versus dihydrodichlorofluorescein and dihydrorhodamine 123. *J Fluoresc* 14, 17-23 (2004).
26. Schilling, S. et al. Glutaminyl cyclase inhibition attenuates pyroglutamate Abeta and Alzheimer's disease-like pathology. *Nat. Med.* 14, 1106-1111 (2008).
27. He, W. & Barrow, C. J. The A beta 3-pyroglutamyl and 11-pyroglutamyl peptides found in senile plaque have greater beta-sheet forming and aggregation propensities in vitro than full-length A beta. *Biochemistry* 38, 10871-10877 (1999).
28. Walsh, D. M. et al. Naturally secreted oligomers of amyloid beta protein potently inhibit hippocampal long-term potentiation in vivo. *Nature* 416, 535-539 (2002).

The invention claimed is:

1. An isolated antibody, or fragment thereof, that specifically binds to a region in an Aβ-peptide capable of being nitrated, wherein said antibody, or fragment thereof, is produced according to a method comprising the steps of
   a) affinity purification of a serum containing antibodies using a nitrated Aβ-peptide coupled to a chromatography column, or screening an sc-Fv phage display library using a nitrated Aβ-peptide, and
   b) optionally following step a) with a further purification step through exclusion of binding to a non-nitrated Aβ-peptide;
   wherein said antibody is a monoclonal, polyclonal, human, humanized, and/or recombinant antibody or a functional fragment thereof, and wherein said antibody specifically binds to an Aβ peptide that is nitrated at position 10 and does not bind to an Aβ peptide that is not nitrated at position 10.

2. A pharmaceutical composition or formulation, comprising an isolated antibody, or a fragment thereof, that binds to an Aβ peptide that is nitrated at position 10 and does not bind to an Aβ peptide that is not nitrated at position 10, together with a pharmaceutically acceptable carrier, excipient, and/or stabilizer.

3. A diagnostic kit, comprising:
   an anit-body or fragment thereof according to claim 1;
   optionally together with additional auxiliary agents for performing a method for determining the status and/or progression of the aggregation of amyloid-β peptide (Aβ).

4. The isolated antibody, or fragment thereof, according to claim 1, which binds to a Aβ peptide having a 3' nitrotyrosine at position 10.

* * * * *

UNITED STATES PATENT AND TRADEMARK OFFICE
CERTIFICATE OF CORRECTION

| | | |
|---|---|---|
| PATENT NO. | : 9,011,862 B2 | Page 1 of 1 |
| APPLICATION NO. | : 13/383521 | |
| DATED | : April 21, 2015 | |
| INVENTOR(S) | : Michael Thomas Heneka et al. | |

It is certified that error appears in the above-identified patent and that said Letters Patent is hereby corrected as shown below:

In the specification

Column 10,
Line 29, "FIGS. 2A-2E" should read --Figures 2A-2F--.

Signed and Sealed this
Twenty-second Day of December, 2015

Michelle K. Lee
*Director of the United States Patent and Trademark Office*